(12) United States Patent
Carlsen et al.

(10) Patent No.: US 6,769,430 B1
(45) Date of Patent: Aug. 3, 2004

(54) HEAT AND MOISTURE EXCHANGER ADAPTOR FOR CLOSED SUCTION CATHETER ASSEMBLY AND SYSTEM CONTAINING THE SAME

(75) Inventors: Wayne D. Carlsen, West Jordan, UT (US); Chet M. Crump, Draper, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 191 days.

(21) Appl. No.: 09/702,376

(22) Filed: Oct. 31, 2000

(51) Int. Cl.[7] .................................................. A62B 18/08
(52) U.S. Cl. ............................ 128/201.13; 128/203.16; 128/203.26; 128/204.17; 128/207.14
(58) Field of Search ................................. 604/523, 533, 604/534, 535, 537, 538, 905, 284, 19, 508; 128/201.13, 205.27, 202.27, 912, 207.14, 203.26, 204.17, 203.16

(56) References Cited

U.S. PATENT DOCUMENTS

| | | |
|---|---|---|
| 3,556,097 A | 1/1971 | Wallace |
| 3,782,083 A | 1/1974 | Rosenberg |
| 3,815,754 A | 6/1974 | Rosenberg |
| 3,825,001 A | 7/1974 | Bennet et al. |
| 3,831,629 A | 8/1974 | Mackal et al. |
| 3,834,388 A | 9/1974 | Sauer |
| 3,881,482 A | 5/1975 | Lindholm |
| 3,902,500 A | 9/1975 | Dryden |
| 3,932,153 A | 1/1976 | Byrns |
| 3,937,220 A | 2/1976 | Coyne |
| 3,991,762 A | 11/1976 | Radford |
| 4,009,720 A | 3/1977 | Crandall |
| 4,015,336 A | 4/1977 | Johnson |
| 4,036,616 A | 7/1977 | Byrns |
| 4,047,527 A | 9/1977 | Kelsen |
| 4,062,363 A | 12/1977 | Bonner, Jr. |
| 4,090,513 A | 5/1978 | Togawa |
| 4,159,954 A | 7/1979 | Gangemi |
| 4,193,406 A | 3/1980 | Jinotti |
| 4,291,691 A | 9/1981 | Cabal et al. |
| 4,315,505 A | 2/1982 | Crandall et al. |
| 4,327,723 A | 5/1982 | Frankhouser |
| 4,351,328 A | 9/1982 | Bodai |
| 4,405,163 A | 9/1983 | Voges et al. |
| 4,468,224 A | 8/1984 | Enzmann et al. |
| 4,508,533 A * | 4/1985 | Abramson ................... 604/35 |
| 4,516,573 A | 5/1985 | Gedeon |
| 4,569,344 A | 2/1986 | Palmer |

(List continued on next page.)

FOREIGN PATENT DOCUMENTS

| | | |
|---|---|---|
| EP | 0265163 A2 | 8/1988 |
| EP | 0730878 A2 | 9/1996 |
| WO | WO9721386 | 6/1997 |
| WO | WO9903525 | 1/1999 |
| WO | WO9960954 | 12/1999 |
| WO | WO0002610 | 1/2000 |
| WO | WO0145779 A1 | 6/2001 |
| WO | WO0172365 A1 | 10/2001 |

OTHER PUBLICATIONS

English language Abstract of EP 0 730 878A2.
U.S. patent application No. 09/702,375, filed Oct. 31, 2000.

(List continued on next page.)

*Primary Examiner*—Glenn K. Dawson
*Assistant Examiner*—Darwin P Erezo
(74) *Attorney, Agent, or Firm*—Dority & Manning, P.A.

(57) ABSTRACT

A heat and moisture exchanger (HME) adaptor for a closed suction catheter assembly having one end in communication with a closed suction catheter assembly and another end configured to engage and releasably hold the HME is disclosed herein. The adaptor may include a retainer having an aperture that engages projections on the HME to releasably secure the adaptor to the HME. The adaptor may include a retaining ring or retaining arms that may be deformed or rotated to engage or disengage the projections from the HME.

30 Claims, 16 Drawing Sheets

U.S. PATENT DOCUMENTS

| | | |
|---|---|---|
| 4,573,965 A | 3/1986 | Russo |
| 4,573,979 A | 3/1986 | Blake |
| 4,574,173 A | 3/1986 | Bennett |
| 4,595,005 A | 6/1986 | Jinotti |
| 4,638,539 A | 1/1987 | Palmer |
| 4,646,733 A | 3/1987 | Stroh et al. |
| 4,649,913 A | 3/1987 | Watson |
| 4,657,008 A | 4/1987 | Broddner et al. |
| 4,669,463 A | 6/1987 | McConnell |
| 4,696,296 A | 9/1987 | Palmer |
| 4,696,305 A | 9/1987 | von Berg |
| 4,705,073 A | 11/1987 | Beck |
| 4,798,676 A | 1/1989 | Matkovich |
| 4,805,611 A | 2/1989 | Hodgkins |
| 4,825,859 A | 5/1989 | Lambert |
| 4,834,726 A | 5/1989 | Lambert |
| 4,836,199 A | 6/1989 | Palmer |
| 4,850,350 A | 7/1989 | Jackson |
| 4,852,563 A | 8/1989 | Gross |
| 4,872,579 A | 10/1989 | Palmer |
| 4,909,248 A | 3/1990 | McLennan Anderson |
| 4,929,426 A | 5/1990 | Bodai et al. |
| 4,938,741 A | 7/1990 | Lambert |
| 4,946,445 A * | 8/1990 | Lynn .......................... 604/192 |
| 4,967,743 A | 11/1990 | Lambert |
| 4,969,878 A | 11/1990 | Schmidt et al. |
| D312,880 S | 12/1990 | Bodai et al. |
| 5,029,580 A | 7/1991 | Radford et al. |
| 5,042,468 A | 8/1991 | Lambert |
| D321,252 S | 10/1991 | Jepson et al. |
| 5,060,646 A | 10/1991 | Page |
| 5,067,496 A | 11/1991 | Eisele |
| 5,073,164 A | 12/1991 | Hollister et al. |
| 5,083,561 A | 1/1992 | Russo |
| 5,088,486 A | 2/1992 | Jinotti |
| 5,101,817 A * | 4/1992 | Etter ..................... 128/200.26 |
| 5,104,389 A | 4/1992 | Deem et al. |
| 5,107,829 A | 4/1992 | Lambert |
| 5,109,471 A | 4/1992 | Lang |
| 5,125,893 A | 6/1992 | Dryden |
| 5,134,996 A | 8/1992 | Bell |
| 5,139,018 A | 8/1992 | Brodsky et al. |
| 5,140,983 A | 8/1992 | Jinotti |
| 5,158,569 A | 10/1992 | Strickland et al. |
| 5,184,611 A | 2/1993 | Turnbull |
| 5,191,881 A | 3/1993 | Beck |
| 5,195,527 A | 3/1993 | Hicks |
| 5,201,309 A | 4/1993 | Friberg et al. |
| 5,201,717 A * | 4/1993 | Wyatt et al. ................ 604/192 |
| 5,213,096 A | 5/1993 | Kihlberg et al. |
| 5,215,522 A | 6/1993 | Page et al. |
| 5,220,916 A | 6/1993 | Russo |
| 5,230,332 A | 7/1993 | Strickland |
| 5,242,084 A | 9/1993 | Jinotti |
| 5,254,098 A | 10/1993 | Ulrich et al. |
| 5,255,676 A | 10/1993 | Russo |
| 5,277,177 A | 1/1994 | Page et al. |
| 5,300,043 A | 4/1994 | Devlin et al. |
| 5,309,902 A | 5/1994 | Kee et al. |
| 5,309,904 A | 5/1994 | Beck |
| 5,325,850 A | 7/1994 | Ulrich et al. |
| 5,325,851 A | 7/1994 | Reynolds et al. |
| 5,333,606 A | 8/1994 | Schneider et al. |
| 5,333,607 A | 8/1994 | Kee et al. |
| 5,337,780 A | 8/1994 | Kee |
| 5,343,857 A | 9/1994 | Schneider et al. |
| 5,346,478 A | 9/1994 | Jinotti |
| 5,349,950 A | 9/1994 | Ulrich et al. |
| 5,354,267 A | 10/1994 | Niermann et al. |
| 5,355,876 A | 10/1994 | Brodsky et al. |
| 5,357,946 A | 10/1994 | Kee et al. |
| 5,368,017 A | 11/1994 | Sorenson et al. |
| 5,370,610 A | 12/1994 | Reynolds |
| 5,383,447 A | 1/1995 | Lang |
| 5,390,668 A | 2/1995 | Lehman |
| 5,390,669 A * | 2/1995 | Stuart et al. ............ 128/207.14 |
| 5,435,298 A | 7/1995 | Anthony |
| 5,445,141 A | 8/1995 | Kee et al. |
| 5,449,348 A | 9/1995 | Dryden |
| 5,460,172 A | 10/1995 | Eckerbom et al. |
| 5,460,176 A | 10/1995 | Frigger |
| 5,460,613 A | 10/1995 | Ulrich et al. |
| 5,487,381 A | 1/1996 | Jinotti |
| 5,490,503 A | 2/1996 | Hollister |
| 5,496,287 A | 3/1996 | Jinotti |
| 5,513,627 A | 5/1996 | Flam |
| 5,513,628 A | 5/1996 | Coles et al. |
| D373,637 S | 9/1996 | Spearman |
| 5,578,006 A | 11/1996 | Schön |
| 5,582,161 A | 12/1996 | Kee |
| 5,582,165 A | 12/1996 | Bryan et al. |
| 5,590,644 A | 1/1997 | Rosenkoetter |
| 5,598,840 A | 2/1997 | Iund et al. |
| 5,605,149 A | 2/1997 | Warters |
| 5,628,306 A | 5/1997 | Kee |
| 5,642,726 A | 7/1997 | Owens et al. |
| 5,664,564 A | 9/1997 | Palmer |
| 5,664,594 A | 9/1997 | Kee |
| 5,676,136 A | 10/1997 | Russo |
| 5,687,714 A | 11/1997 | Kolobow et al. |
| 5,701,891 A | 12/1997 | Groenke |
| 5,715,815 A | 2/1998 | Lorenzen et al. |
| D393,722 S | 4/1998 | Fangrow, Jr. et al. |
| 5,735,271 A | 4/1998 | Lorenzen et al. |
| 5,769,702 A | 6/1998 | Hanson |
| 5,775,325 A | 7/1998 | Russo |
| 5,813,402 A | 9/1998 | Jinotti |
| 5,855,562 A | 1/1999 | Moore et al. |
| 5,882,348 A | 3/1999 | Winterton et al. |
| 5,906,201 A | 5/1999 | Nilson |
| 5,919,174 A | 7/1999 | Hanson |
| 5,992,413 A | 11/1999 | Martin, Jr. et al. |
| 6,033,455 A | 3/2000 | Kurashima |
| 6,095,135 A | 8/2000 | Clawson et al. |
| 6,105,576 A | 8/2000 | Clawson et al. |
| 6,131,573 A | 10/2000 | Brown |
| 6,165,168 A | 12/2000 | Russo |
| 6,227,200 B1 | 5/2001 | Crump et al. |
| 6,248,099 B1 | 6/2001 | Bell |
| 6,363,930 B1 * | 4/2002 | Clawson et al. ....... 128/201.13 |
| 6,422,235 B1 | 7/2002 | Persson |

OTHER PUBLICATIONS

International Search Report Oct. 3, 2002.

Written Opinion, Jul. 31, 2003.

U.S. patent application No. 09/459,522 (BAL–64), Filed Dec. 13, 1999.

U.S. patent application No. 09/471,317 (BAL–55), Filed Dec. 23, 1999.

U.S. patent application No. 09/693,261 (BAL–66–CIP–CON), Filed Oct. 20, 2000.

U.S. patent application No. 10/082,786 (BAL–113), Filed Feb. 25, 2002.

U.S. patent application No. 09/716,486 (BAL–66–CON), Filed Nov. 20, 2000.

U.S. patent application No. 09/741,769 (KCX–384), Filed Dec. 19, 2000.

* cited by examiner

SECTION 7-7

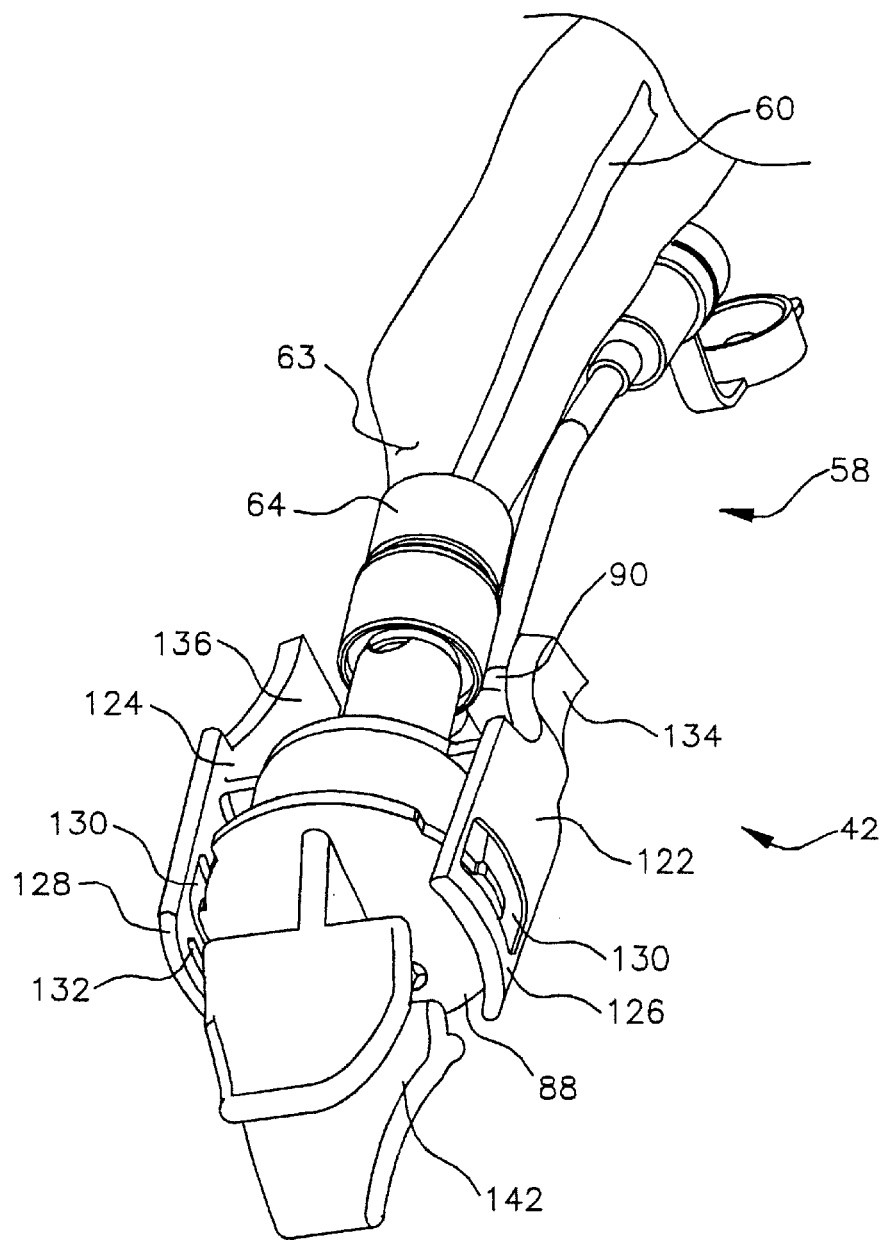
FIG. 15.A

HEAT AND MOISTURE EXCHANGER ADAPTOR FOR CLOSED SUCTION CATHETER ASSEMBLY AND SYSTEM CONTAINING THE SAME

FIELD OF THE INVENTION

The present invention relates generally to respiratory catheter systems utilizing a heat and moisture exchanger, and particularly to an adaptor for use in such systems.

BACKGROUND OF THE INVENTION

There are a number of different circumstances in which it is necessary for a person to have an artificial airway, such as a tracheostomy tube, placed in his or her respiratory tract. As used herein, the phrase "artificial airway" includes devices such as tracheostomy tubes, endotracheal tubes and the like. Artificial airways keep the patient's natural airway open so that adequate lung ventilation can be maintained. In particular situations, the artificial airway must be left in the patient for a prolonged period of time. For example, many persons suffering severe neck or head trauma use a tracheostomy tube in conjunction with mechanical ventilation during extended recovery and rehabilitation periods.

When an artificial airway is used, it is critical that respiratory secretions be periodically removed. This is typically accomplished by the use of a respiratory suction catheter that is advanced into and through the tracheostomy tube. As the suction catheter is withdrawn, a negative pressure (or vacuum) is applied to draw mucus and other secretions from the patient's airways and the interior of the artificial airway. While a substantial amount of mucus and other secretions will be withdrawn through the lumen of the suction catheter, a portion of the mucus and other secretions will remain as a film on the outside of the catheter.

In a closed suction catheter assembly (for example as set forth in U.S. Pat. Nos. 3,991,762 and 4,569,344), the catheter may be enveloped by a protective sleeve and include a valve mechanism disposed near the vacuum source. These features reduce the risk of contamination to both the patient and the care-giver.

In normal breathing, the structures of the nose and sinus passages serve to heat and moisturize inhaled air. In situations where a patient requires mechanical ventilation on a periodic basis, it is common to place a heat and moisture exchanger (HME) on the proximal end of the artificial airway after removal of the mechanical ventilator. This type of placement is commonly done with patients who are able to breathe on their own for an extended period of time. In such systems and as used herein, "proximal" refers to the direction toward the clinician and "distal" refers to the direction toward the patient.

The HME is intended to replicate these functions, of heating and moisturizing air, in patients having artificial airways. The HME is adapted to reduce heat and moisture loss from the respiratory system of the patient as the patient breathes. This is done by retaining within the HME heat and moisture from air which is exhaled through the HME, and by warming and moisturizing air that is inhaled through the HME. The HME typically includes a material, such as porous foam, that is enclosed within a housing or other structure.

To date, most HMEs have not been used in conjunction with a closed suction catheter assembly. Thus, prior to suctioning respiratory secretions from a patient, it may be necessary to remove the HME from the proximal end of the artificial airway so that a suctioning catheter may be advanced to the patient's natural airways. Removal and attachment of the HME often causes discomfort to the patient and, during the period in which the HME has been removed, the patient is deprived of heat and moisture exchange and may be deprived of supplemental oxygen, if used.

Thus, there is a need for an inexpensive adaptor that enables a closed suction catheter to be easily and quickly attached to and removed from an HME that is mounted to an artificial airway while minimizing patient discomfort.

SUMMARY OF THE INVENTION

Various features and advantages of the invention will be set forth in part in the following description, or may be obvious from the description, or may be learned through practice of the invention.

The present invention is generally directed to an adaptor for connecting a closed suction catheter assembly to an HME mounted on an artificial airway, such as a tracheostomy tube. In addition, the present invention is directed to a closed suction catheter system containing the adaptor and a closed suction catheter assembly. The adaptor of the present invention does not interfere with patient breathing.

The adaptor has a first end that is adapted to be in communication with the closed suction catheter assembly. The adaptor may be removably or non-removably engaged with the catheter assembly. The adaptor also has a second end which is adapted to engage the heat and moisture exchanger. Further, there is a channel formed through the adaptor. This channel allows an aspirating catheter of the closed suction catheter assembly to be moved through the adaptor. The aspirating catheter can then also be moved through an aperture formed through the heat and moisture exchanger.

An adaptor cover may also be provided for use with the closed suction catheter system. The cover is configured to selectively isolate the closed suction catheter assembly from the environment, and to facilitate cleaning of the catheter after suctioning.

The present invention may also provide an alternative embodiment of an adaptor for connecting a closed suction catheter assembly to an HME. The adaptor includes a first end configured for attachment to a closed suction catheter assembly, and a second end including a retainer capable of engaging the HME. The adaptor is configured for advancement of a catheter therethrough. The retainer may include a ring, for example a circular or elliptical ring member, having a wall configured to encircle and releasably engage the HME.

Furthermore, if a ring retainer is included in the adaptor, the ring may include a pair of oppositely disposed apertures located on first and second portions of the ring. The apertures are configured to engage the HME. Moreover, the retaining ring may also include bowed outward third and fourth portions oppositely disposed from each other on the ring with the bowed outward third and fourth portions disposed between the first and second portions on the ring. These bowed third and fourth portions may be configured such that, as they are urged inwardly toward each other, the first and second portions are urged to move outwardly away from the HME, thereby disengaging the first and second portions from the HME.

The retainer of the adaptor may be formed such that the first portion and the second portion are defined by apertures for receiving external projections of the HME. Alternatively, the retainer may include at least one L-shaped channel configured for receiving external projections of the HME. In one embodiment, the adaptor may also include an annular projection configured for engaging a valve in the top of the HME.

The present invention may also form an adaptor assembly for connecting a closed suction catheter assembly to an HME. The adaptor assembly includes an adaptor having a first end configured for attachment to a closed suction catheter assembly; and a second end including a retainer configured for engaging the HME and positioning the closed suction catheter assembly with respect to the HME. The adaptor is configured for advancement of a catheter therethrough. The adaptor assembly may also contain an annular projection defining a channel through which a catheter of the closed suction catheter assembly may be advanced. The adaptor assembly may also include an adaptor cover configured for attachment to the annular projection.

The adaptor cover can take on various configurations. For example, the cover may have a cylindrical wall formed therein with at least one opening formed in the wall. A cap may be provided with the cover for covering the opening.

In another embodiment, the adaptor assembly includes at least one arm formed in the retainer, wherein the arm is capable of engaging the HME. For example, the retainer may include at least two arms oppositely disposed from each other wherein each arm is capable of engaging the HME.

In addition, at least one arm may include an aperture capable of receiving a projection of the HME. Furthermore, at least one arm may include a surface member capable of engaging the HME. The adaptor assembly may include a base formed in the retainer wherein each arm is pivotally connected to a base.

The present invention is also directed to a closed suction catheter system. This system includes a closed suction catheter assembly having a catheter and a protective sleeve enveloping the catheter. The closed suction catheter assembly includes a distal end; and an adaptor connected to this distal end capable of engaging a proximal end of an HME.

BRIEF DESCRIPTION OF THE DRAWINGS

FIG. 15A is a perspective view of the adaptor cover of FIG. 15 shown attached to the adaptor of the embodiment of FIG. 11.

DETAILED DESCRIPTION

Figure 1:
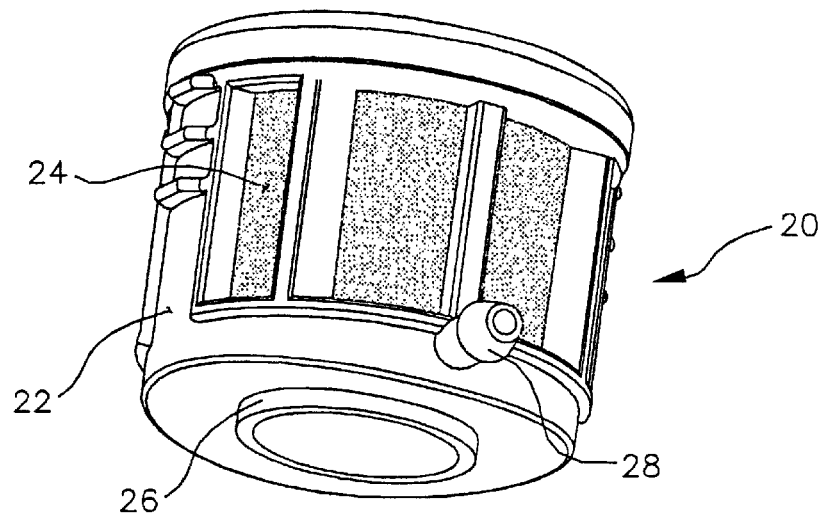
FIG. 1 is a perspective view of a heat and moisture exchanger (HME) in accordance with the teachings of the prior art.

Reference will now be made in detail to embodiments of the invention, one or more examples of which are shown in the drawings. It should be appreciated that each example is provided by way of explaining the invention, and not as a limitation of the invention. For example, features illustrated or described with respect to one embodiment may be used with another embodiment to yield still a further embodiment. Such modifications and variations are within the scope and spirit of the invention.

The invention relates to a closed suction catheter assembly. At its distal end, which is the end nearest the patient once a closed suction catheter is attached, the closed suction catheter may be attached to an artificial airway via one of a variety of connectors, including, for example, a multi-legged tracheostomy connector. One of the legs of the tracheostomy connector may be connected to a tracheostomy tube. With the use of the closed suction catheter assembly, the ventilating circuit need not be detached from the patient during suctioning, and a single catheter may be used for an extended period, typically a 24-hour period. The patient may need to have the air drawn in through the artificial airway heated and moistened since air is no longer traveling through the nose, sinuses, or throat. To accomplish this task, it is commonly the case that a heat and moisture exchanger be placed in the respiratory system.

A representative heat and moisture exchanger (HME) is shown in FIG. 1 at 20. As illustrated therein, the HME includes a housing 22 with a porous material 24 disposed within the housing. The porous material 24 is designed to reduce heat and moisture loss as the patient breathes. Heat and moisture within exhaled air is retained within the porous material 24. The inhaled air is warmed and humidified as the inhaled air passes through the porous material 24. The porous material 24 is typically a foam material that has sufficient porosity to reduce the loss of heat and moisture from the patient. The material is sometimes treated with a hygroscopic salt to enhance performance. The housing 22 includes a bottom port 26 for receiving an exposed end of a tracheostomy tube or other artificial airway.

The HME 20 also includes a side port 28 that may connect to an oxygen supply line to administer oxygen to the patient. Oxygen may be required by those, for instance, with emphysema and other diseases that cause damage to the lung tissue.

Figure 2:
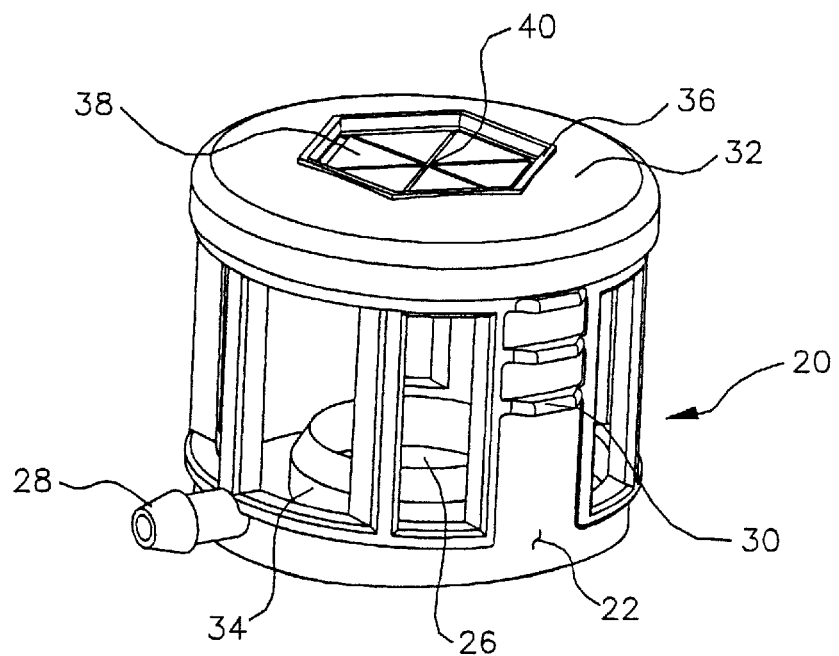
FIG. 2 is a perspective view of another HME in accordance with the teachings of the prior art.

FIG. 2 shows an additional conventional heat and moisture exchanger that is available from Datex-Ohmeda of Helsinki, Finland. The HME, generally indicated again at 20, includes a housing 22 having ridges 30, and a top surface 32 that forms the upper portion of the housing 22. In some embodiments, the top surface 32 is configured as a removable cover that engages the housing 22. The ridges 30 enable a clinician to securely hold the housing while the housing 22 is being attached to or removed from a tracheostomy tube or other artificial airway. The housing 22 also includes an enclosure 34 into which material, such as the material 24, may be placed. The housing 22 further includes a bottom port 26, which is used to connect the HME 20 to a tracheostomy tube or other artificial airway. Further, the HME 20 may include a side port 28.

Disposed in alignment with the bottom port 26 is a top port 36 that is positioned in the center of the top surface 32. The bottom port 26 and the top port 36 are ends of a control aperture. The top port 36 is covered by a plurality of triangular-shaped projections 38 which are pivotably attach to the top surface 32 to enclose the top port 36 and form a valve 40. During attachment of the HME to an adaptor 42 (described in greater detail below), an annular projection of the adaptor 44 (see FIGS. 3, 5, and 9) contacts the triangular-shaped projections 38 causing the projections 38 to be deflected away from the annular projection 44 and open the valve 40. The projections 38 may be deflected toward either the enclosure 34 of the housing 22 or away from the housing 22. Thus, in practice, a clinician can suction a patient using the HME 20 by advancing a catheter (not shown) through the top port 36 and into the tracheostomy tube or artificial airway (not shown).

Figure 3:
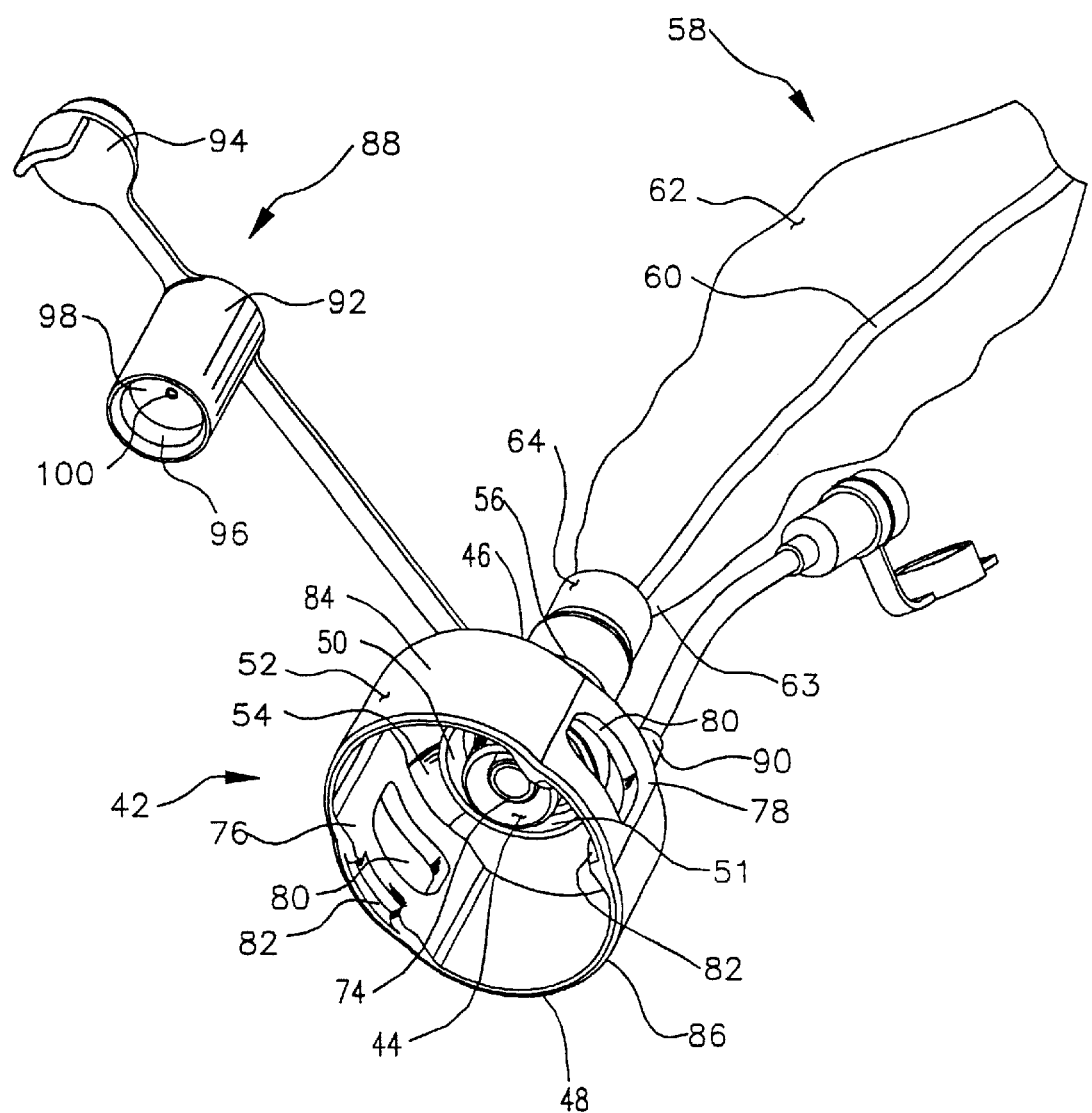
FIG. 3 is a perspective view of an adaptor of the present invention.

FIG. 3 shows a perspective view of an adaptor, generally indicated at 42, made in accordance with the principles of the present invention. The adaptor 42 has a proximal side 46 that is the side of the adaptor 42 that is attached to a closed suction catheter assembly 58. The adaptor 42 may be an integral or non-removable component of the catheter assembly 58 or can be configured to be releasably engaged to the closed suction catheter assembly 58 by means commonly known in the art. The adaptor 42 also has a distal side 48 that is configured for attachment to an HME (not shown).

Figure 14:
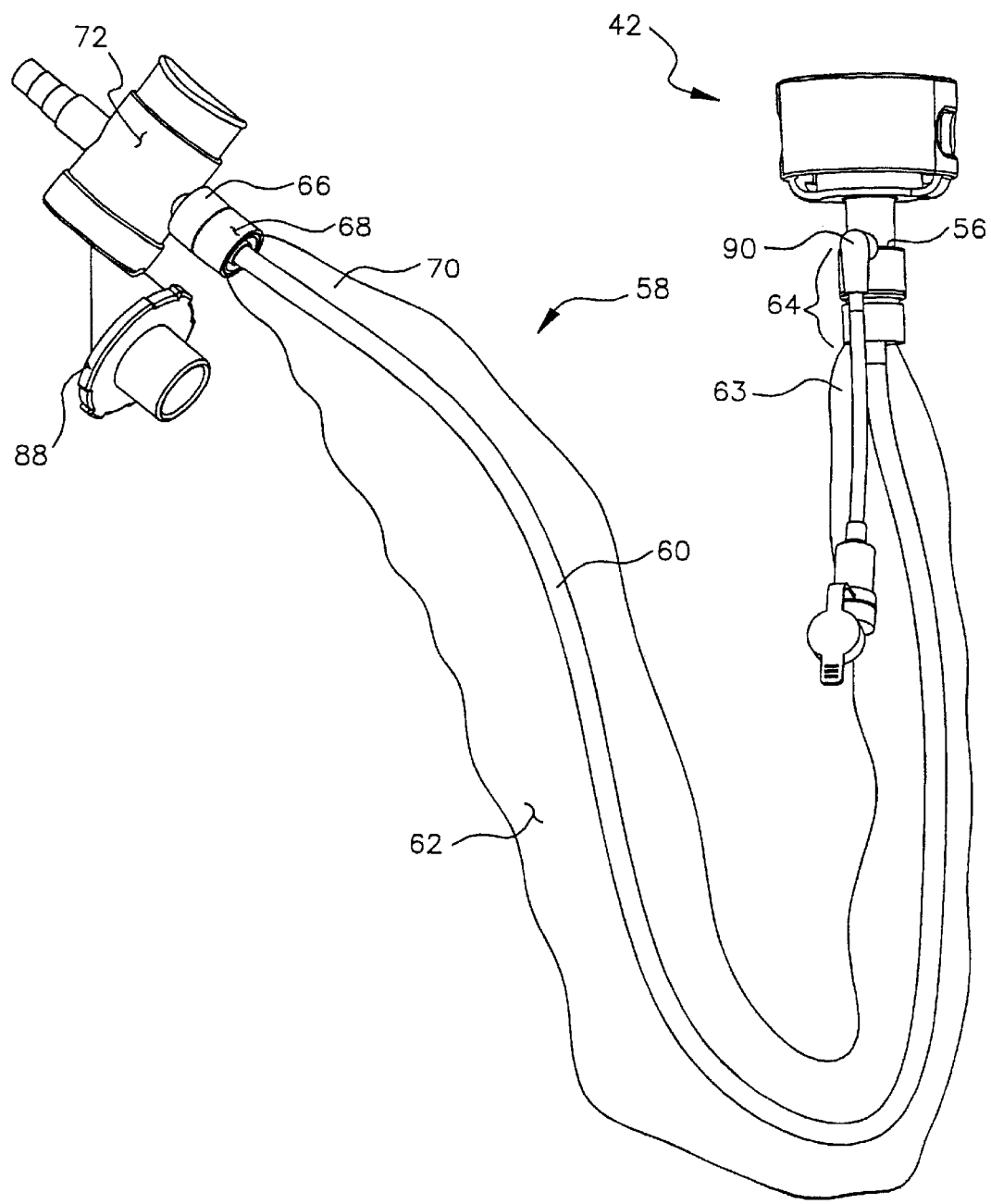
FIG. 14 is a side view of a closed suction catheter system with an adaptor and an adaptor cover.

The adaptor 42 includes a base 50 and a retaining structure configured with the base. In this embodiment, the retaining structure is a retainer 52 attached to the base 50 by at least two arms 54. As shown in FIG. 3, the retainer 52 takes the form of a retaining ring. The base 50, in turn, is connected to the distal end 56 of the closed suction catheter assembly 58. The closed suction catheter assembly 58 is shown fully in FIG. 14 and is partially shown in FIG. 3. The assembly includes an elongated aspirating catheter 60, an elongated protective sleeve 62 surrounding the catheter 60, and a coupling 64 which receives catheter 60 and secures the distal end 63 of the protective sleeve 62, thereby sealing the protective sleeve 62 about the catheter 60. The catheter 60 can be advanced through the coupling 64 and into an artificial airway such as a tracheostomy tube (not shown) of a patient to suction mucus and other secretions from the patient's respiratory system. The closed suction catheter assembly 58 also includes, as shown in FIG. 14, a proximal end 66 and a proximal coupling 68 which retains the proximal end 70 of the protective sleeve 62 in position. The closed suction catheter assembly 58 also includes a valve mechanism 72 for selectively supplying suction through elongate aspirating catheter 60.

Referring now to FIG. 3, an annular projection 44 is disposed on the distal side 51 of base 50. The annular projection 44 surrounds a channel 74 through which the aspirating catheter 60 is advanced. As will be explained in more detail below, the annular projection 44 extends through the valve 40 (FIG. 2) of the HME 20 when the adaptor 42 is attached to the HME 20. Thus, the annular projection 44 is configured to hold open the projections 38 (FIG. 2). Such a configuration reduces the risk of mucus accumulating in HME 20, as the projections 38 are sufficiently distant from the catheter 60 so that mucus is not removed from the catheter 60 by the projections 38. If mucus accumulates in and is allowed to remain in the HME 20, it may interfere with the patient's breathing.

In one embodiment, the retainer 52 may be an annular or elliptical wall and form four sections. As shown in FIG. 3, two of the four sections of the retainer 52, a first section 76 and a second section 78, are disposed on opposing sides of the retainer 52 and may be provided with an attachment mechanism 80 for attaching the retainer 52 to the HME (not shown). In the embodiment shown in FIG. 3, the retaining mechanism 80 is an aperture 80 that is formed in the first and second sections 76 and 78, respectively, of the retainer 52. The apertures 80 are sized to engage the ridges 30 of the HME 20. In some embodiments, a guide notch 82 (shown in FIG. 3) may be formed in first and second sections 76 and 78, respectively, to help guide the ridges 30 into the aperture 80. Once the ridges 30 are retained by the apertures 80, the adaptor 42 is securely attached to the HME 20.

The two remaining sections of the retainer 52 may include, in selected embodiments, a third section 84 and a fourth section 86 which, as shown in FIG. 3, may be bowed outwardly and away from first and second sections 76 and 78, respectively. The third section 84 and the fourth section 86 are situated between the first and second sections 76 and 78, respectively. When the clinician desires to remove the adaptor 42 from the HME 20, he or she needs only to press the third and fourth sections 84 and 86, respectively, toward each other. This forces the retainer 52 to deform slightly and causes the first and second sections 76 and 78, respectively, to move outwardly and away from the HME 20. Movement of the sections 76 and 78 causes the apertures 80 to move a sufficient distance away from the ridges 30 so that the ridges 30 are no longer nested therein and engaged thereby. Thus, the retainer 52 can be removed from the HME 20 without torque or force being applied to the HME or the artificial airway. The ability to remove the closed suction catheter assembly 58 without applying any torque to the artificial airway is important, as a small amount of torque can cause irritation and discomfort to the patient. In some instances, the closed suction catheter assembly may be used numerous times a day. In these instances, a small amount of irritation can lead to increased patient discomfort.

Because the closed suction catheter assembly 58 may often be removed, an adaptor cover 88 may be provided. When the catheter assembly 58 is removed, it is important that the catheter assembly 58 be properly cleaned prior to removal via the lavage port 90. It is also important that the aspirating catheter 60 be positioned within the channel 74 when the catheter assembly 58 is removed from the patient. Even if the aspirating catheter 60 extends out of the channel 74 and has not been cleaned properly, the use of an adaptor cover 88 can help to prevent contamination of the aspirating catheter 60.

As shown in FIG. 3, an exemplary adaptor cover 88 may be formed to include a first portion 92 and an end cap 94. The first portion 92 includes an elongated cylinder 96 with a wall 98 formed through the middle of the cylinder. A small opening 100 may be formed in the wall 98 to allow a very small amount of air into the first portion 92. Thus, the first portion 92 may be attached to the annular projection 44 after removal of the closed suction catheter assembly 58 after each suctioning procedure. If the adaptor 42 is fixed to the catheter assembly 58, then cover 88 must be configured so that first portion 92 has a sufficient length to extend into the adaptor 42. Once the aspirating catheter 60 has been cleaned, the end cap 94 may further be used to cover the opening 100 in the first valve portion 92.

Figure 4:
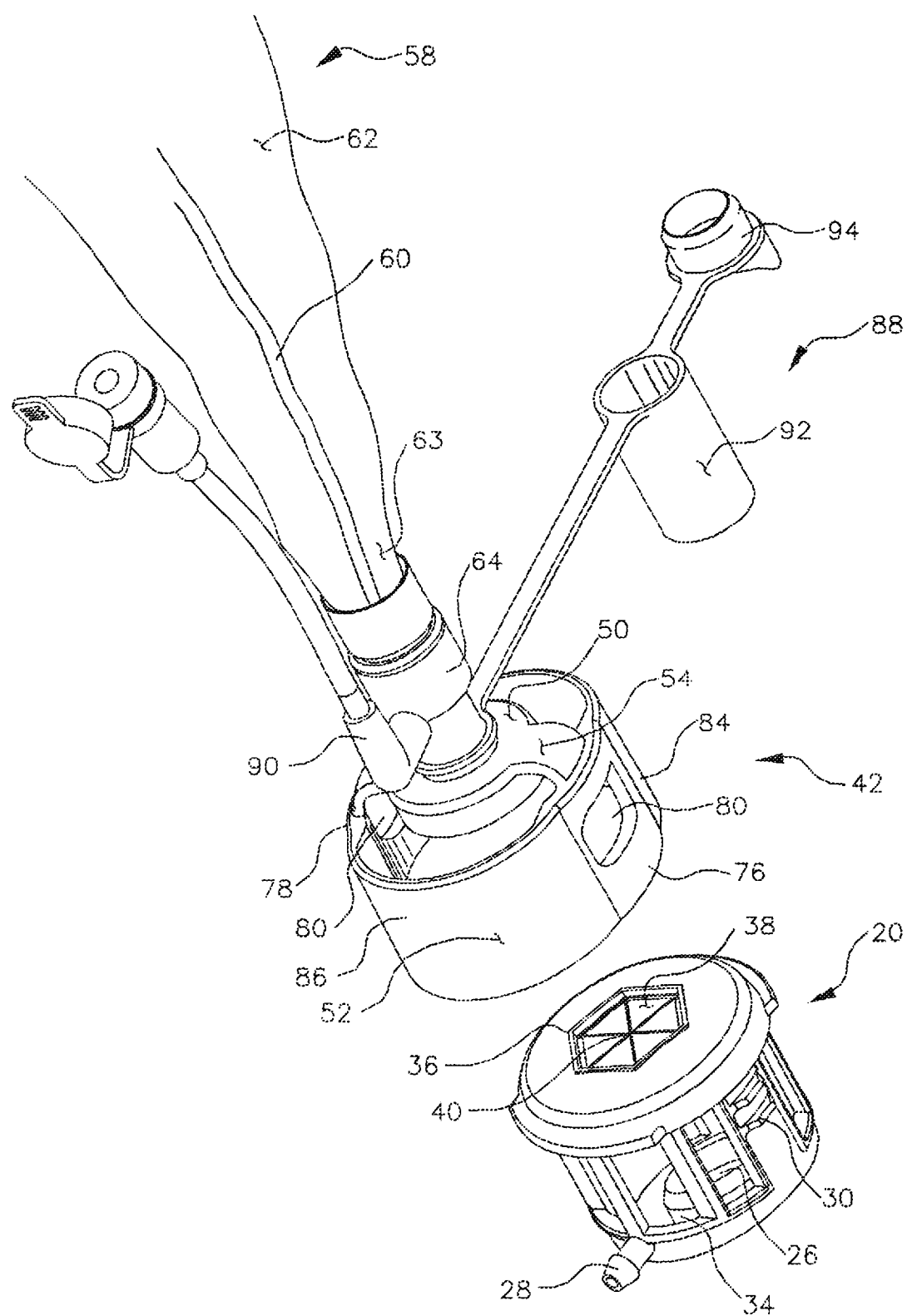
FIG. 4 is another perspective view of the adaptor shown in FIG. 3 in conjunction with an HME.
Figure 5:
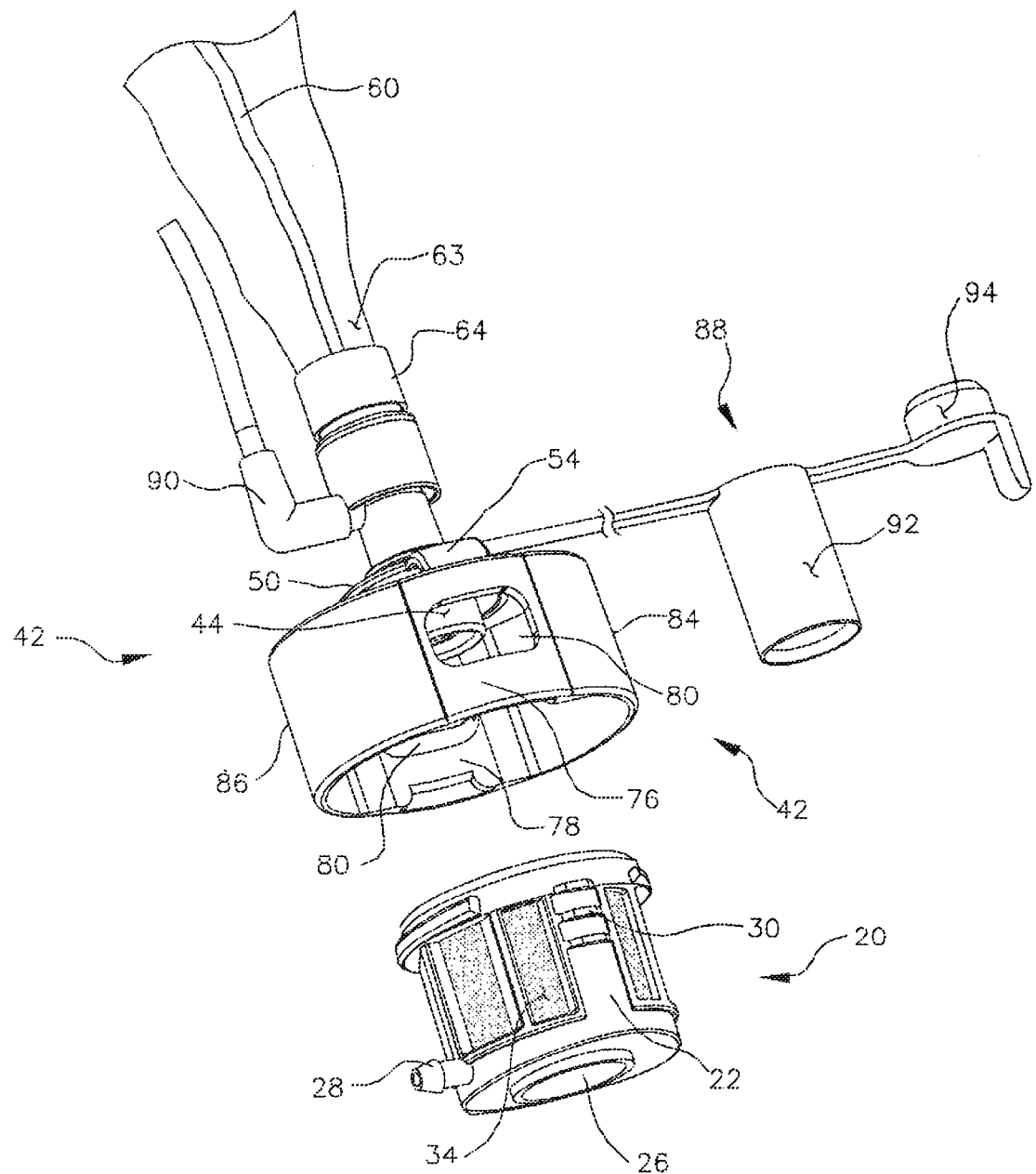
FIG. 5 is a perspective view of an HME and an adaptor positioned with respect to each other so that they may be easily connected to one another.

FIG. 4 shows a perspective view of the adaptor 42 and the HME 20 from the proximal or care-giver end of the closed-suction catheter assembly 58. FIG. 5 shows a close-up side view of the orientation of the adaptor 42 and the HME 20. FIGS. 4 and 5 show the alignment between the ridges 30 of the HME 20 and the apertures 80 of the retaining ring 52 of the adaptor 42. With the ridges 30 and the retaining ring 52 in alignment with each other, the adaptor 42 need only be moved downwardly until the ridges 30 snap into the apertures 80 for the HME 20 to be held securely to the adaptor 42. The clinician may assist this process by pressing the third and fourth sections 84 and 86, respectively, toward each other to enable the ridges 30 to more easily engage the apertures 80. Alternatively, the housing 22 of the HME 20 may be flexed to slightly deform the housing 22 to enable the ridges 30 to more easily engage the apertures 80. Once the ridges 30 are retained within the apertures 80, the housing may be allowed to return to its original position.

To release the adaptor 42 from the HME 20, the third and fourth sections 84 and 86, respectively, of the retaining ring 52 need only be squeezed momentarily to move the first and second sections 76 and 78, respectively, outwardly. This movement releases the ridges 30 from the apertures 80 and allows HME 20 to be disengaged from the adaptor 42.

Figure 6:
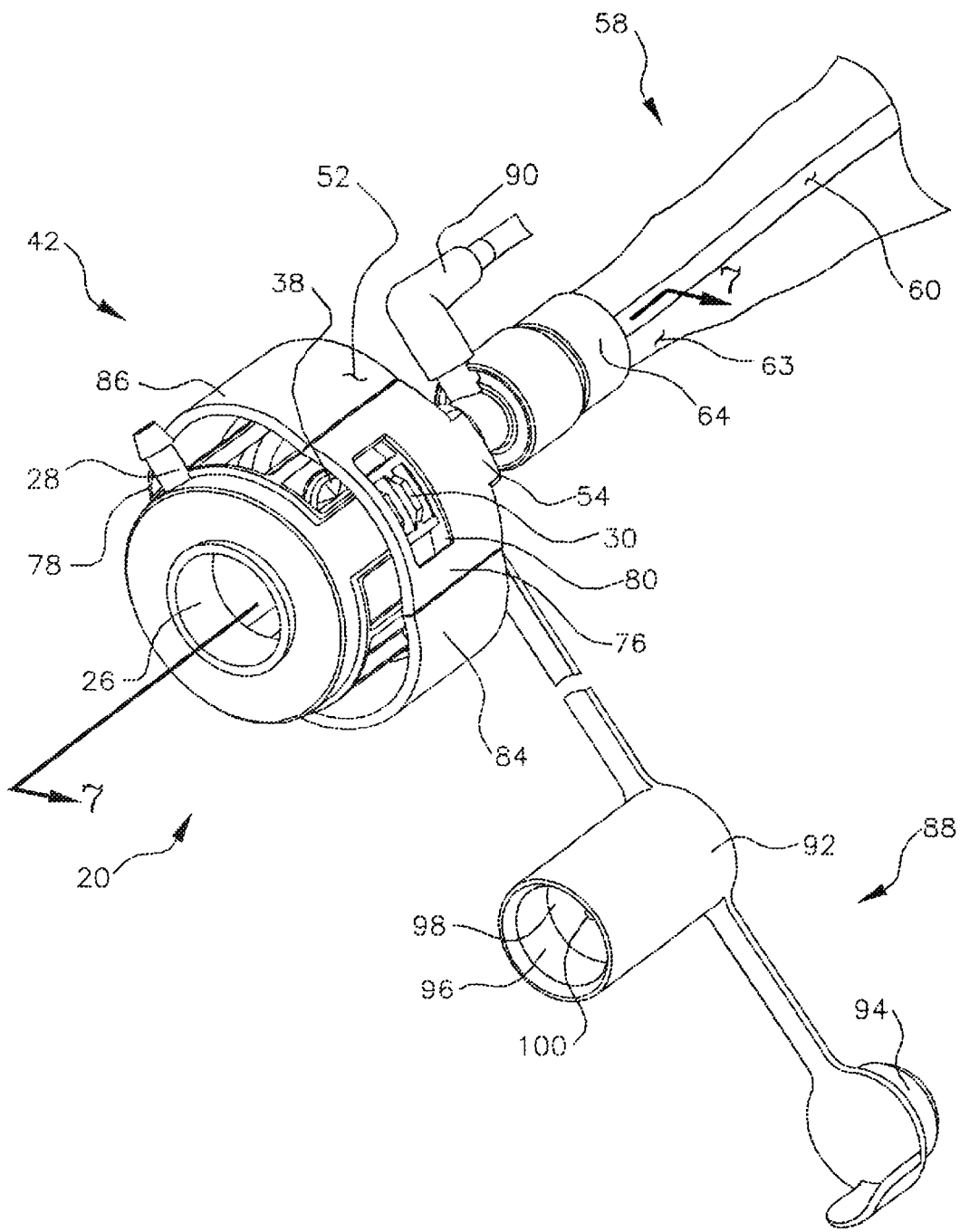
FIG. 6 is a perspective view of the adaptor shown in FIG. 5 with the HME nested within the adaptor.

FIG. 6 is a close-up perspective view of the HME 20 seated within and engaged to the adaptor 42. As shown therein, the ridges 30 of the HME 20 are nested in the apertures 80 in the first and second sections 76 and 78, respectively, so that the retaining ring 52 is held securely to the HME 20. Because the apertures 80 in the retaining ring 52 are wider than the ridges 30, the adaptor 42 is able to rotate slightly in either direction. If desired, the apertures 80 could be made virtually the same size as the area covered by ridges 30 to reduce or prevent such rotation.

Figure 7:
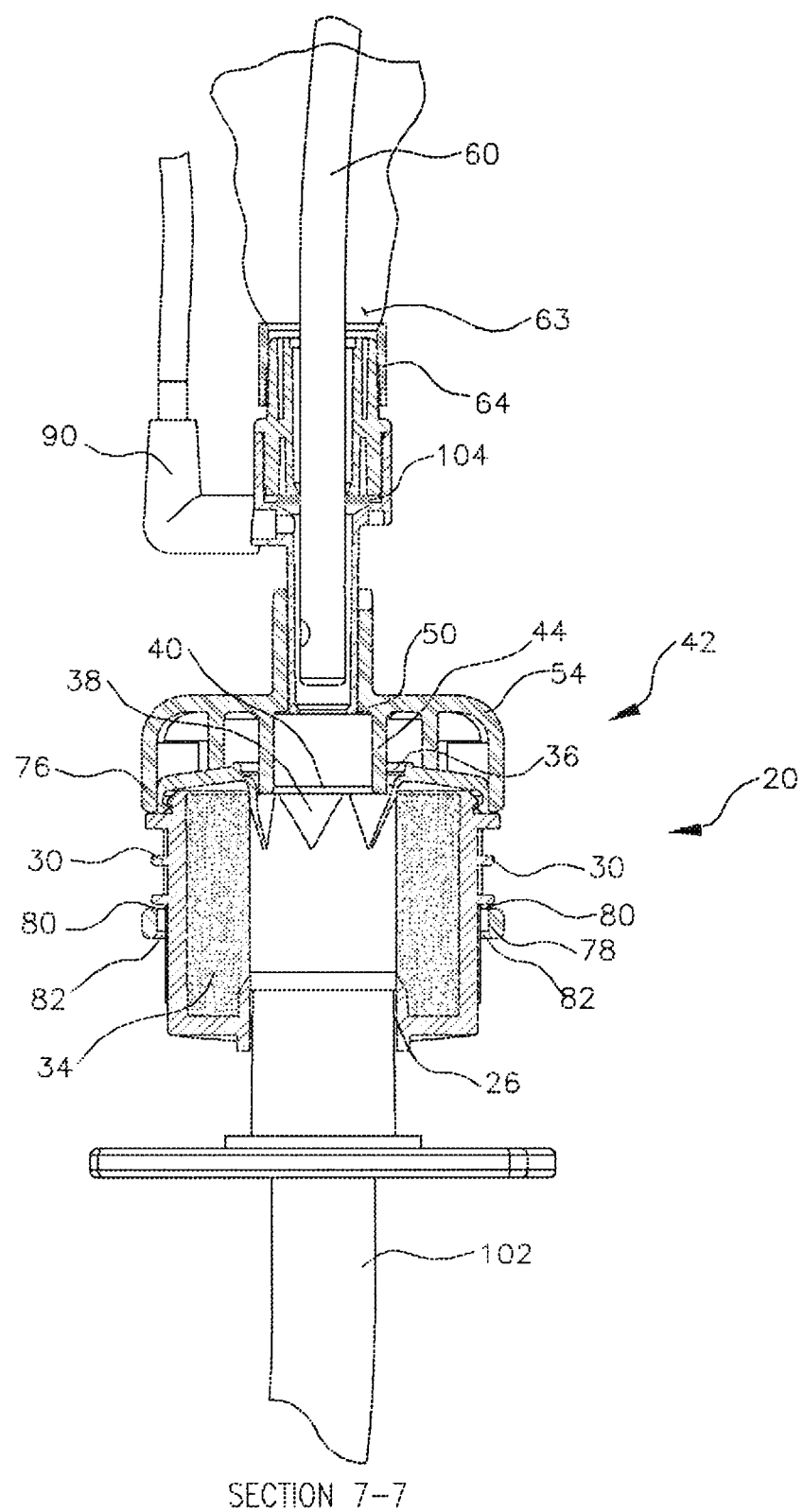
FIG. 7 is a partial cross-sectional view of the adaptor and HME shown in FIG. 6 taken along line 7—7 of FIG. 6, wherein the HME is mounted on an artificial airway, the artificial airway not being shown in FIG. 6.

FIG. 7 is a side partial cross-sectional view of the HME 20 and the adaptor 42 taken along line 7—7 in FIG. 6 through the ridges 30 and the apertures 80, as well as a fragmented view of the HME mounted on a tracheostomy tube 102. The adaptor cover 88 is not shown in this view. As shown in FIG. 3, the annular projection 44 is configured to engage the projections 38 of the valve 40 of the HME 20 so that the projections are moved to an "open" position, which is shown in FIG. 7, upon attachment of the adaptor 42 to the HME 20. If the projections 38 were to engage the aspirating catheter 60 as it is retracted from the tracheostomy tube 102, mucus and other secretions could be scraped from the aspirating catheter 60 by the projections 38. Such secretions would remain in the HME 20 and could drip back into the tracheostomy tube or coat the porous material 34 in the HME 20 and potentially interfere with the patient's breathing. By keeping the projections 38 in the "open" position, the annular projection 44 allows the mucus to remain on the aspirating catheter 60 until the aspirating catheter 60 engages a seal 104 of the closed suction catheter assembly 58. The seal 104, as shown in FIG. 7, is disposed within the closed suction catheter assembly 58 and engages the aspirating catheter 60 as the catheter is moved through the center of the annular seal 104. Mucus is stripped from the aspirating catheter 60 by the seal 104 as the aspirating catheter passes through the center of the annular seal 104.

Figure 8:
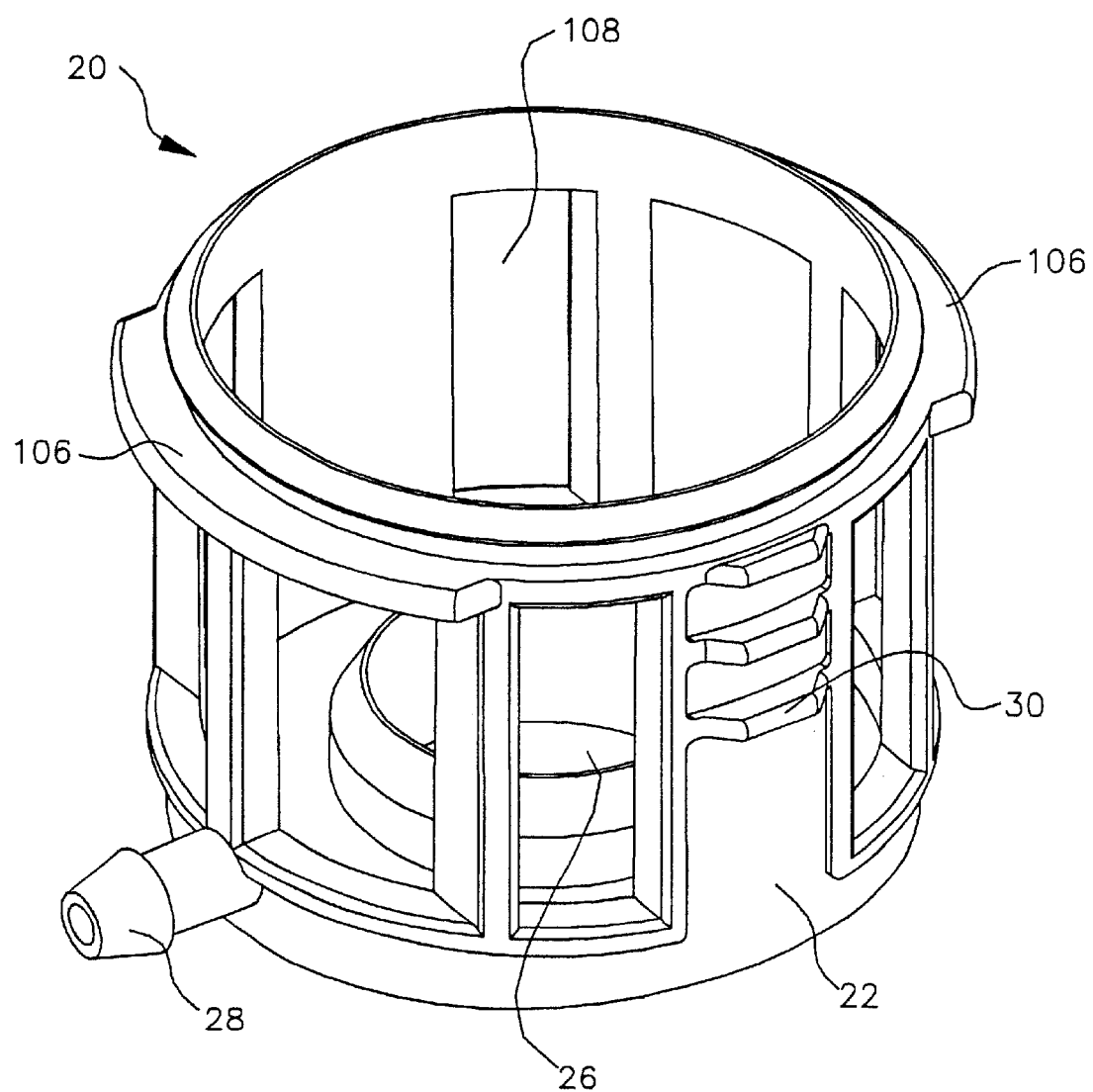
FIG. 8 is a perspective view of an HME with the cover of the housing removed.

FIG. 8 shows a perspective view of an HME 20 having a removable top surface or cover. The HME 20 shown in FIG. 8 includes a pair of flange keys 106 that are disposed near the top opening 108 of the HME 20, the flange keys 106 being disposed oppositely from each other along the exterior of the HME 20. The flange keys 106 may be offset from the ridges 30. For example and as shown in FIG. 8, the flange keys 106 may be offset 90 degrees from the ridges 30. The flange keys 106 may be configured to fit between the HME housing 22 and the third and fourth sections 84 and 86, respectively, of the retaining ring 52 when the adaptor 42 is attached to the HME 20. The flange keys 106 help to prevent the clinician or care giver from inadvertently orienting the adaptor 42 on the HME 20 so that the apertures 80 of the retaining ring 52 are not aligned with the ridges 30. If the retaining ring 52 is not in the proper orientation, the first and second sections 76 and 78, respectively, will engage the flange keys 106 and prevent improper attachment of the HME 20 to the adaptor 42.

While discussed with respect to FIGS. 4 through 8 as being a retaining ring, those skilled in the art will appreciate that the retainer 52 need not be in the form of a ring. For example, the third and fourth sections 84 and 86, respectively, could be omitted from the retainer. In such an embodiment, the first and second sections 76 and 78, respectively, will engage the HME 20. In such a configuration, a flange may be provided on each of the first and second sections 76 and 78, respectively. The flange would permit the first and second sections 76 and 78, respectively, to be urged away from the HME 20 when the closed suction catheter assembly 58 is to be disengaged from the HME 20.

Figure 9:
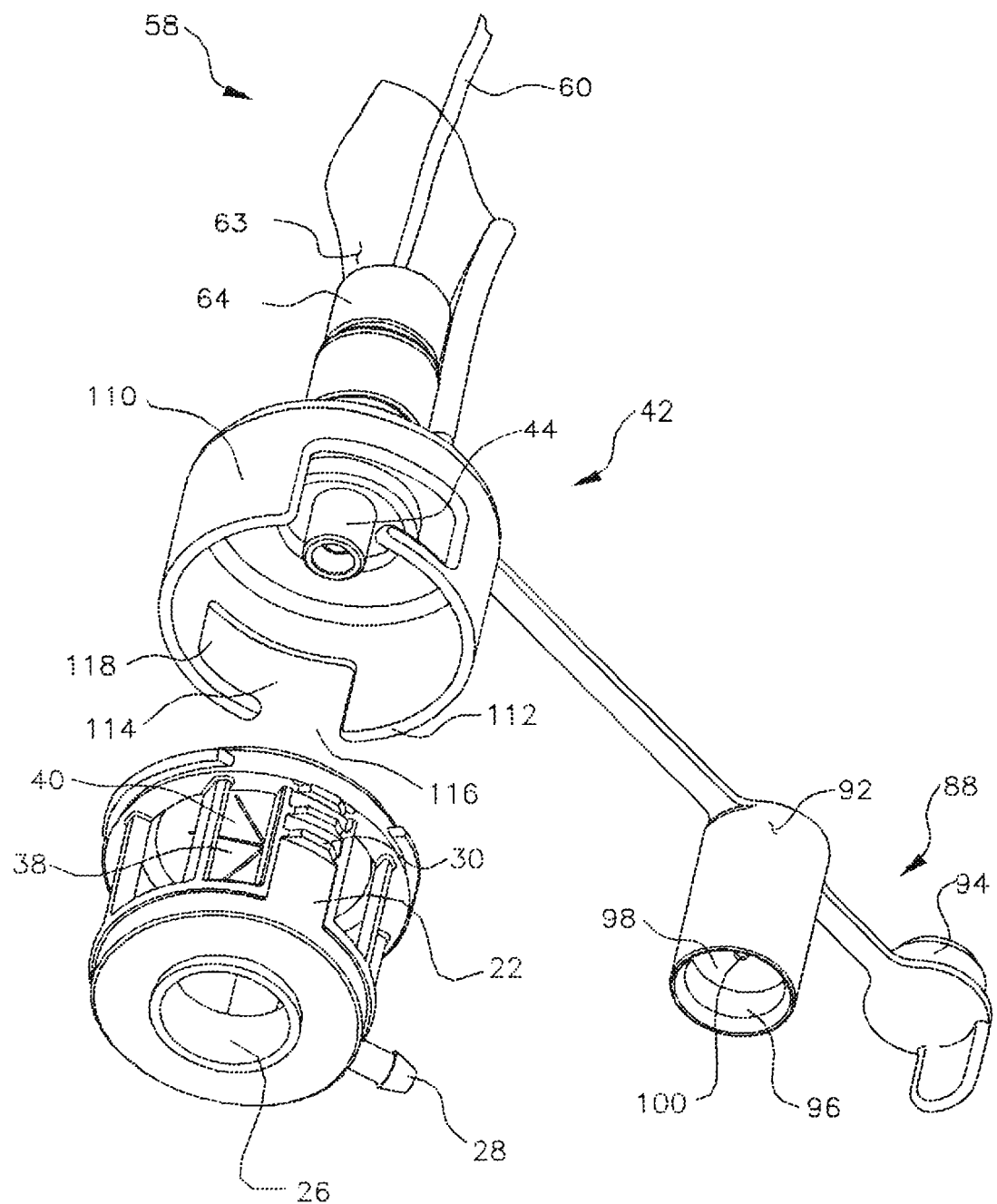
FIG. 9 is a perspective view of an alternate embodiment of an adaptor made in accordance with the present invention.

Turning now to FIG. 9, there is shown therein a perspective view of an alternative embodiment of an HME adaptor, generally indicated at 42, made in accordance with the principles of the present invention. As illustrated in FIG. 9, the retainer may be formed as a cup-shaped housing 110, the distal portion 112 of the housing 110 forming a retaining ring for encircling the HME 20. An L-shaped port or channel 114 extends into the housing 110 to receive the ridges 30.

Figure 10:
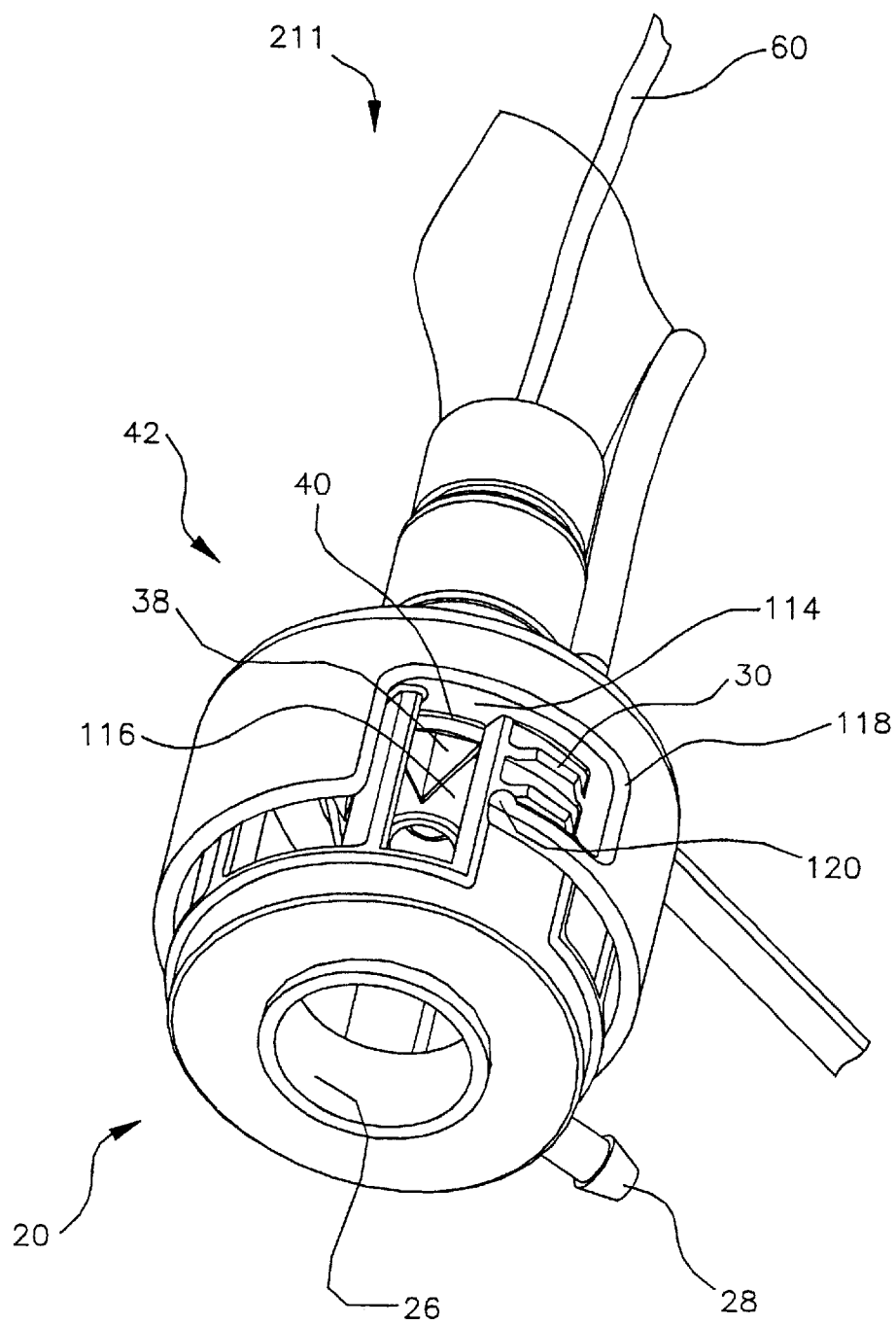
FIG. 10 is a perspective view of the invention shown in FIG. 9 with the adaptor mounted on the HME.

In the embodiment depicted in FIG. 9, the ridges 30 are initially aligned with the first end 116 of the L-shaped channel 114. Once the ridges 30 have been sufficiently advanced into the L-shaped channel 114, the cup-shaped housing 110 can be rotated to place the ridges 30 at the second end 118 of the channel 114, as shown in FIG. 10. Once the ridges 30 are secured at the end 118 of L-shaped channel 114, the closed suction catheter assembly 58 can be used in the conventional manner.

The ridges 30 at the end 118 of the channel 114 may be maintained in place in a variety of ways, including friction, or a lip 120 (FIG. 10) or another mechanism which inhibits inadvertent counter-rotation and thus removal of the ridges 30 from the channel 114. FIG. 10 illustrates the interlocking arrangement of the HME 20 and the adaptor 42. Those skilled in the art will appreciate that there are numerous holding mechanisms that can be used in such a channel. These include, but are not limited to, a nonlinear path within the channel, a skid resistant surface along some portion of the channel, as well as a snap-fit or press-fit engagement between the channel and the ridges 30.

As with the embodiments shown in FIGS. 3 and 9, adaptor 42 includes an annular projection 44 through which the aspirating catheter 60 may be advanced. The annular projection 44 holds open the projections 38 that form the valve 40 in the HME 20, thus preventing mucus from being deposited in the HME 20.

Figure 11:
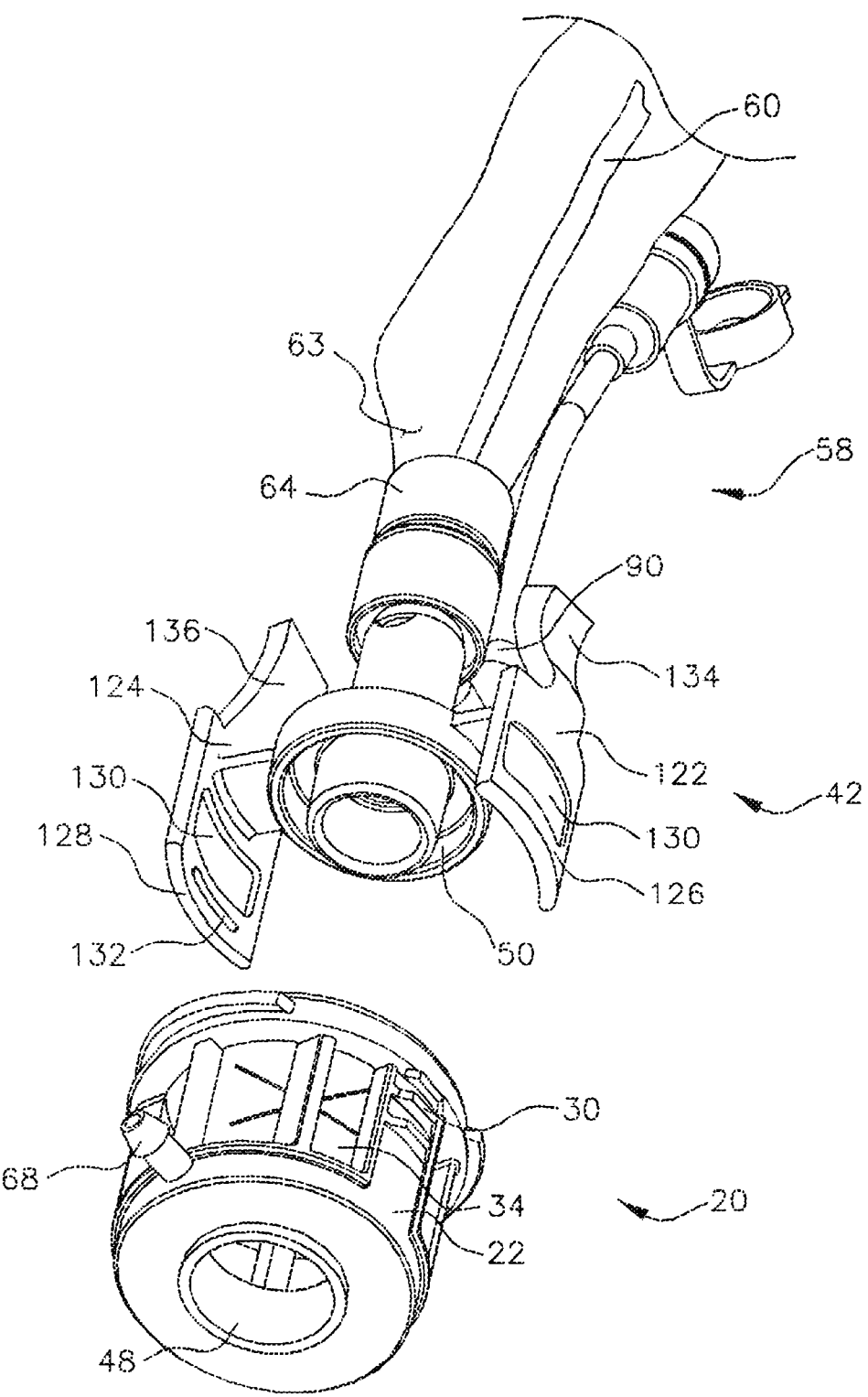
FIG. 11 is a perspective view of yet another embodiment of an adaptor made in accordance with the present invention.

Turning now to FIG. 11, there is shown an alternate embodiment of an HME adaptor 42 made in accordance with the principles of the present invention. The adaptor 42 is disposed at the distal end of the closed section catheter assembly 58. The adaptor 42 includes a retainer formed by first and second arms 122 and 124, respectively, which are pivotally attached to the base 50. A distal portion 126 and 128 of each arm 122 and 124, respectively, extends in the distal direction (toward the patient) away from the base 50. The distal portions 126 and 128 of each arm provides a mechanism for holding the closed suction catheter assembly 58 to the HME 20. Although a wide variety of mechanisms may be used to hold the catheter assembly 58 to the HME 20, the embodiment shown in FIG. 11 utilizes a pair of apertures 130 formed in the first and second arms 122 and 124, respectively, to receive the ridges 30 of the HME 20. Other mechanisms that may be suitable include placing a high friction material, shown at 132 in FIG. 11, such as rubber, to provide frictional engagement between the housing 22 of the HME 20 and the adaptor 42.

A pair of proximal portions 134 and 136 of the first and second arms 122 and 124, respectively, extend away from the base 50 in the proximal or clinician direction, and provide levers for pivoting the first and second arms 122 and 124, respectively, away from the HME housing 22. To ensure a secure fit between the HME 20 and the adaptor 42, the arms 122 and 124 may be biased toward each other so that the distance between the distal ends 128 and 126 of the arms may be smaller than the diameter of the HME housing 22. When configured in this manner, the arms 122 and 124 will firmly engage the HME 20 and help to reduce accidental dislocation of the HME 20.

Figure 12:
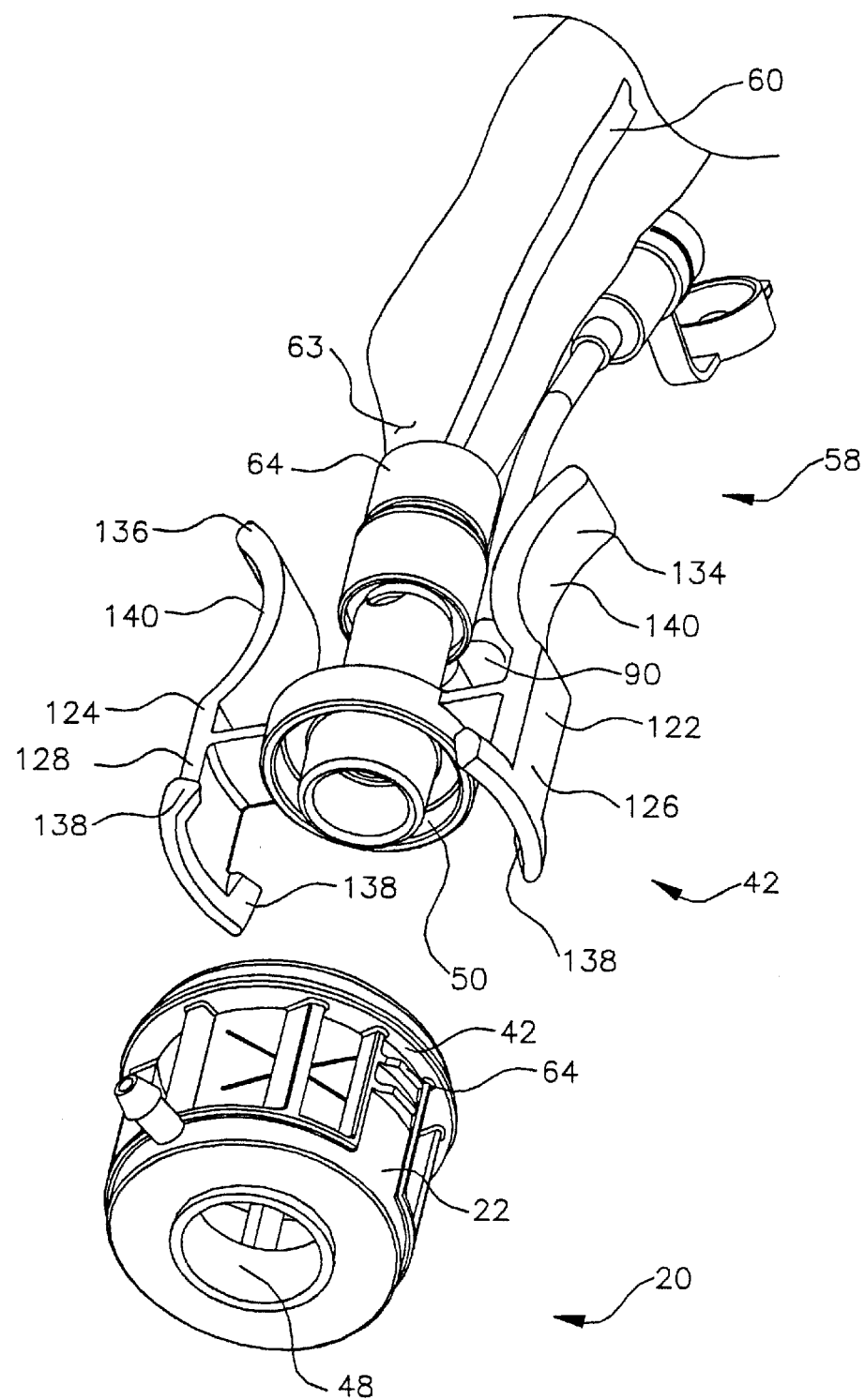
FIG. 12 is a perspective view of another embodiment of the invention wherein the arms of the adaptor are equipped with projections or barbs for engaging the housing of the HME.
Figure 13:
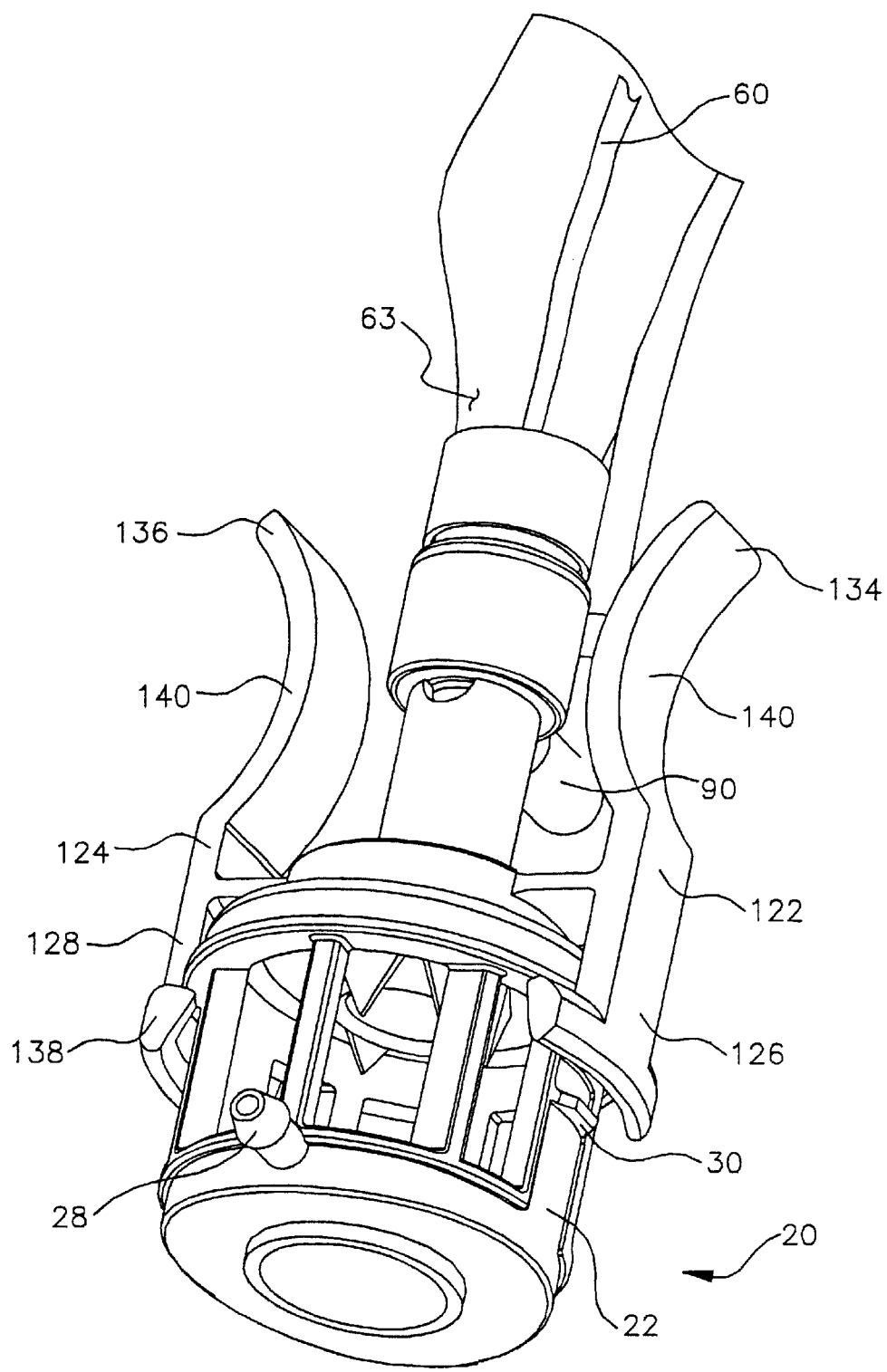
FIG. 13 is a perspective view of the embodiment described in FIG. 12 mounted on an HME.

FIG. 12 and FIG. 13 show a perspective view of yet another embodiment of the HME adaptor 42 that is attached to a closed suction catheter assembly 58 and an HME 20. The closed suction catheter assembly 58 is configured similarly to those shown in FIGS. 5 and 11 and is therefore numbered accordingly.

The adaptor 42 includes a retainer formed by a first arm 122 and a second arm 124 that are pivotally attached to the base 50. The distal portion 126 and 128 of each arm 122 and 124, respectively, may have one or more barbs or projections 138, which are configured to engage the housing 22 of the HME 20. The projections 138 nest in the HME housing 22 to secure the adaptor 42 to the HME 20.

Each arm 122 and 124 has a proximal portion 134 and 136, respectively, which is disposed on the end which is opposite of the distal portion of each of the respective arms. By pressing the proximal sections 134 and 136 toward each other, the distal portions 126 and 128 of the arms 122 and 124, respectively, and the accompanying projections 138, can be moved away from each other to enable the adaptor 42 to move relative to the HME 20. Each of proximal sections 134 and 136 may have a concave portion 140 or may be otherwise shaped to facilitate gripping by the care-giver for receiving the fingers of the clinician. For example, the clinician may place his or her thumb in one concave portion 140 and forefinger in the opposing concave portion. By pressing the thumb toward the forefinger, the proximal portions 134 and 136 are moved together and the distal portions of the arms 126 and 128 are moved apart.

To mount the adaptor 42 on the HME 20, the arms 122 and 124 can be pivoted as described above. However, by providing an appropriate taper to the distal end of the projections 138, the arms 122 and 124 can be made to move outwardly as the adaptor is advanced onto the housing. Once the projections 138 pass the upper rim 23 of the housing 22, the projections 138 will return to their original position and secure the catheter assembly 58 to the HME 20.

FIG. 14 shows a side view of a closed suction catheter system containing a closed suction catheter assembly 58 with an HME adaptor 42 and an alternate embodiment of the adaptor cover 88. The cover 88 may be attached to the valve 72 of the closed suction catheter assembly 58, but may be otherwise attached to the closed suction catheter assembly 58. The cover 88 has a first valve portion (not shown) which is substantially the same as the first portion 92 that is shown in FIGS. 3–9. The cover 88 as shown in FIG. 14 allows the closed suction catheter assembly 58 to form a loop with the adaptor 42. When the catheter assembly 58 is not being used, the ability to form the catheter assembly 58 and the adaptor 42 into a loop allows the catheter assembly 58 to be conveniently hung somewhere out of the way of the care-giver and the patient, but available for immediate use. FIG. 14 does not show such a loop, but instead shows cover 88 being unattached to adaptor 42.

Figure 15:
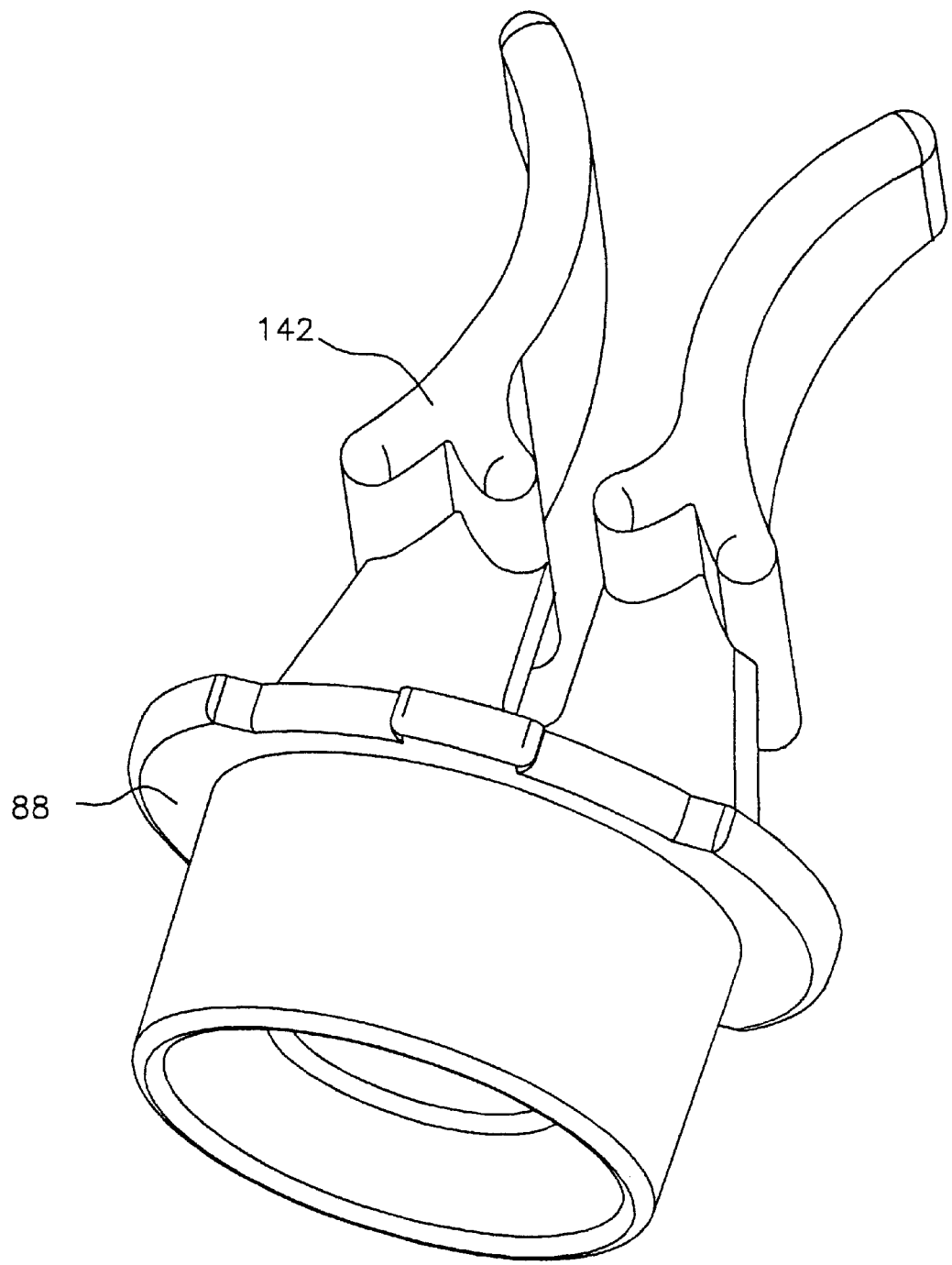
FIG. 15 is a perspective view of an alternate embodiment of an adaptor cover for use with the adaptor of the present invention.

FIG. 15 shows a perspective view of an alternate embodiment of the adaptor cover 88. The cover 88 shown in FIG. 15 covers the annular projection 44 and can be configured to decrease the risk of contamination. The cover 88, as shown therein, also includes a clip 142 that allows the cover 88 to be easily and conveniently attached to and removed from other structures, such as, for example, the protective sleeve 62, the aspirating catheter 60, or to nearby structures, such as, for example, a stand.

FIG. 15A shows the adaptor cover 88 attached to an HME adaptor 42. While the HME adaptor is the embodiment described in FIG. 11, it is to be understood that the adaptor cover 88 can be attached to any embodiment of the present invention.

Figure 16:
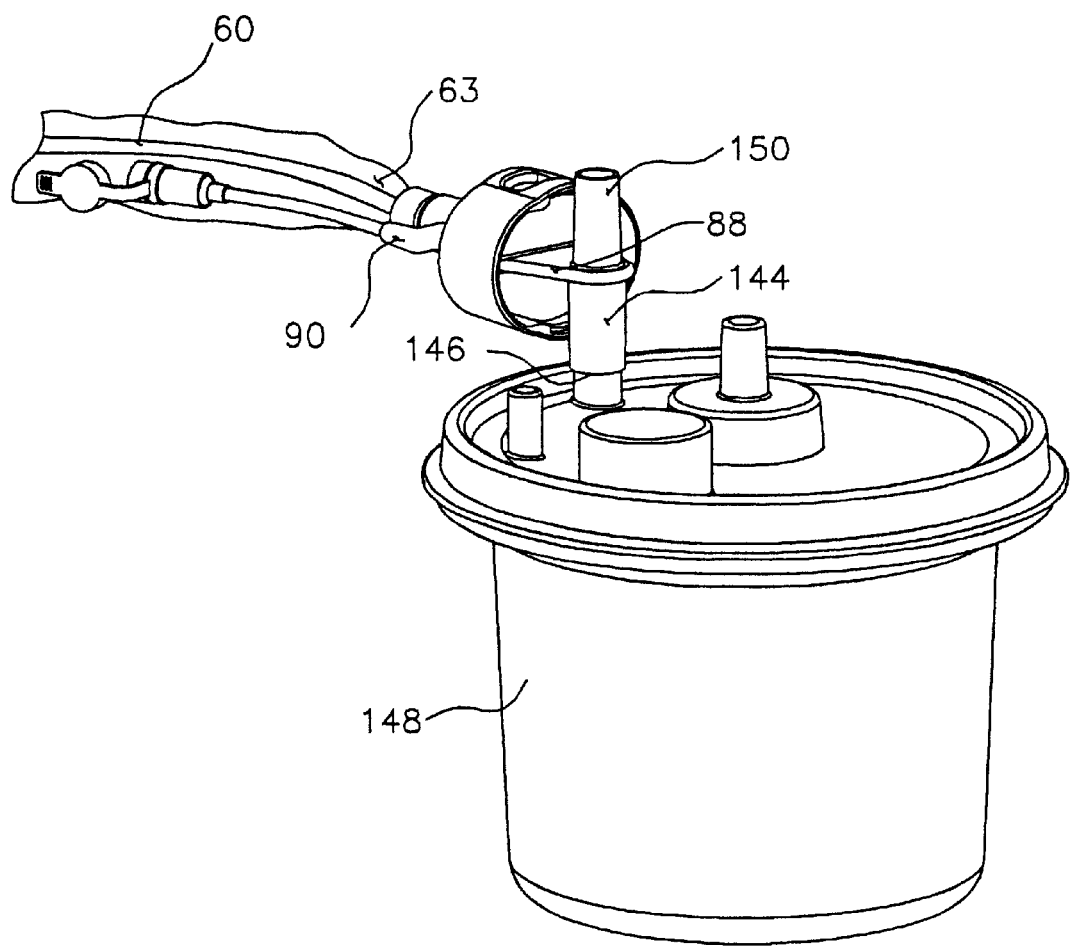
FIG. 16 is a perspective view of yet another embodiment of an adaptor cover for use with the adaptor of the present invention.

Finally, FIG. 16 shows yet another embodiment of the adaptor cover 88 which may be used in accordance with the teachings of the present invention. The adaptor cover 88 shown therein includes a portion that attaches to the annular projection 44 and is geometrically configured in a manner similar to the embodiment of the adaptor cover 88 depicted in FIG. 6. The cover 88 shown in FIG. 16 includes a tube 144 that is configured at a first end 146 for attachment to a suction canister 148. The second end 150 of the tube 144 may be capped, or may have suction tubing or a feed line attached thereto.

While the invention has been described in detail with respect to specific embodiments thereof, it will be appreciated that those skilled in the art, upon attaining an understanding of the foregoing may readily conceive of alterations to, variations of and equivalents to these embodiments. Accordingly, the scope of the present invention should be assessed as that of the appended claims and any equivalents thereto.

What is claimed is:

1. A medical device having an adaptor for connecting a closed suction catheter assembly having an aspirating catheter to a heat and moisture exchanger having an aperture formed therethrough, the medical device comprising:

a heat and moisture exchanger having an aperture formed therethrough;

a closed suction catheter assembly having an aspirating catheter, the aspirating catheter of the closed suction catheter assembly is movable through the aperture of the heat and moisture exchanger; and an adaptor having a first end adapted to be in communication with a distal end of the closed suction catheter assembly having an aspirating catheter, the adaptor having a second end adapted to releasably engage the heat and moisture exchanger having an aperture formed therethrough, the adaptor defining a channel formed through the adaptor so that the aspirating catheter of the closed suction catheter assembly is movable through the adaptor and through the aperture of the heat and moisture exchanger;

wherein at least a portion of the second end is adapted to be moved outwardly from the heat and moisture exchanger in order to effect disengagement of the second end.

2. The medical device according to claim 1, wherein the second end includes a ring having a wall.

3. The medical device according to claim 2, wherein the wall is configured to encircle and receive the heat and moisture exchanger.

4. The medical device according to claim 2, wherein the ring is circular or elliptical.

5. The medical device according to claim 2, wherein the ring further contains a pair of oppositely disposed apertures within the wall, the apertures being configured to engage the heat and moisture exchanger.

6. The medical device according to claim 1, wherein the second end is a retaining ring having:

a first portion and a second portion, the first and second portions oppositely disposed from each other and configured to engage the heat and moisture exchanger; and bowed outward third and fourth portions being oppositely disposed from each other on the ring between the first and second portions of the ring.

7. The medical device according to claim 6, wherein the retaining ring is circular or elliptical, and wherein the third and fourth portions are configured such that, as the third and fourth portions are urged inwardly toward each other, the first and second portions are urged to move outwardly away from the heat and moisture exchanger, thereby disengaging the first and second portions from the heat and moisture exchanger.

8. The medical device according to claim 6, wherein the first and second portions define apertures for receiving external projections of the heat and moisture exchanger.

9. The medical device according to claim 1, wherein said first end is releasably engaged with the distal end of the closed suction catheter assembly.

10. A medical device having an adaptor for connecting a closed suction catheter assembly having an aspirating catheter to a heat and moisture exchanger having an aperture formed therethrough; the medical device comprising:

a heat and moisture exchanger having an aperture formed therethrough, the top of the heat and moisture exchanger having a valve;

a closed suction catheter assembly having an aspirating catheter, the aspirating catheter of the closed suction catheter assembly is movable through the aperture of the heat and moisture exchanger; and an adaptor having a first end adapted to be in communication with a distal end of the closed suction catheter assembly having an aspirating catheter, the adaptor having a second end adapted to releasably engage the heat and moisture exchanger having an aperture formed therethrough, wherein the adaptor defining a channel formed through the adaptor so that the aspirating catheter of the closed suction catheter assembly is movable through the adaptor and through the aperture of the heat and moisture exchanger, wherein the adaptor further comprises an annular projection configured for engaging the valve in the top of the heat and moisture exchanger.

11. A medical device having an adaptor assembly for connecting a closed suction catheter assembly to a heat and moisture exchanger, the medical device comprising:

a heat and moisture exchanger;

a closed suction catheter assembly having an aspirating catheter, the aspirating catheter movable through the heat and moisture exchanger; and an adaptor comprising a first end configured for communication with the closed suction catheter assembly, and a second end configured for engaging the heat and moisture exchanger, the adaptor further comprising a retainer configured to releasably engage the heat and moisture exchanger; the adaptor having an annular projection defining a channel through the adaptor through which the catheter of the closed suction catheter assembly may be advanced; and a cover removably attachable to the annular projection;

wherein at least a portion of the retainer is adapted to be moved outwardly from the heat and moisture exchanger in order to effect disengagement of the second end.

12. The medical device according to claim 11, wherein the cover has a cylindrical wall formed therein.

13. The medical device according to claim 12, wherein the cover further contains at least one opening formed in the cylindrical wall.

14. The assembly according to claim 13, wherein the cover further contains a cap capable of covering the opening.

15. The adaptor assembly according to claim 11, wherein the retainer includes at least one arm formed thereon capable of engaging the heat and moisture exchanger.

16. The adaptor assembly according to claim 11, wherein the retainer comprises at least two arms formed thereon, wherein the arms are disposed oppositely from each other and each of the at least two arms are capable of engaging the heat and moisture exchanger.

17. The adaptor assembly according to claim 16, wherein each of the at least two arms include an aperture capable of receiving a projection of the heat and moisture exchanger.

18. The adaptor assembly according to claim 16, wherein each of the at least two arms include a surface member capable of engaging the heat and moisture exchanger.

19. The adaptor assembly according to claim 16, wherein the retainer further comprises a retainer base, the at least two arms pivotably connected to the retainer base.

20. The adaptor assembly according to claim 11, wherein said first end is releasably engaged with the closed suction catheter assembly.

21. The medical device according to claim 12, wherein said first end is configured to be non-removably fixed to the closed suction catheter assembly.

22. A closed suction catheter system comprising:

a closed suction catheter assembly having a catheter and a protective sleeve enveloping the catheter, the closed suction catheter assembly including a distal end;

a heat and moisture exchanger, the catheter advanceable through the heat and moisture exchanger; and a heat and moisture exchanger adaptor disposed at the distal end of the closed suction catheter assembly, wherein the heat and moisture exchanger adaptor is releasably engageable with the heat and moisture exchanger, such that the catheter is advanceable through the heat and moisture exchanger adaptor and through the attached heat and moisture exchanger.

23. The closed suction catheter system according to claim 22, wherein the heat and moisture exchanger adaptor further comprises a cover.

24. The closed suction catheter system according to claim 22, wherein the heat and moisture exchanger adaptor is releasably engaged with the distal end of the closed suction catheter assembly.

25. The closed suction catheter system according to claim 22, wherein the heat and moisture exchanger adaptor is non-removably fixed at the distal end of the closed suction catheter assembly.

26. A closed suction catheter system comprising:
a closed suction catheter assembly having a catheter and a protective sleeve enveloping the catheter, the closed suction catheter assembly including a distal end;
a heat and moisture exchanger, the catheter advanceable through the heat and moisture exchanger; and
a heat and moisture exchanger adaptor disposed at the distal end of the closed suction catheter assembly, wherein the heat and moisture exchanger adaptor is releasably engageable with the heat and moisture exchanger;
wherein the heat and moisture exchanger adaptor comprises:
a base having a first end in communication with the closed suction catheter assembly, and a second end configured for engaging the heat and moisture exchanger and positioning the closed suction catheter assembly with respect to the heat and moisture exchanger;
a retaining structure configured with the base to releasably engage the base with the heat and moisture exchanger; and
a channel defined through the base so that the catheter of the closed suction catheter assembly is movable through the base and the heat and moisture exchanger and into an artificial airway connected to the heat and moisture exchanger.

27. A closed suction catheter system comprising:
a closed suction catheter assembly having a catheter and a protective sleeve enveloping the catheter, the closed suction catheter assembly including a distal end;
a heat and moisture exchanger, the catheter advanceable through the heat and moisture exchanger, the proximal end of the heat and moisture exchanger having a valve; and
a heat and moisture exchanger adaptor disposed at the distal end of the closed suction catheter assembly, wherein the heat and moisture exchanger adaptor is releasably engageable with the heat and moisture exchanger;
wherein the heat and moisture exchanger adaptor comprises:
a base having a first end in communication with the closed suction catheter assembly, and a second end configured for engaging the heat and moisture exchanger and positioning the closed suction catheter assembly with respect to the heat and moisture exchanger;
a retaining structure configured with the base to releasably engage the base with the heat and moisture exchanger; and
a channel defined through the base so that the catheter of the closed suction catheter assembly is movable through the base and the heat and moisture exchanger and into an artificial airway connected to the heat and moisture exchanger;
wherein the adaptor contains an annular projection configured for engaging a valve in the proximal end of the heat and moisture exchanger.

28. A closed suction catheter system comprising:
a closed suction catheter assembly having a catheter and a protective sleeve enveloping the catheter, the closed suction catheter assembly including a distal end;
a heat and moisture exchanger, the catheter advanceable through the heat and moisture exchanger; and
a heat and moisture exchanger adaptor disposed at the distal end of the closed suction catheter assembly, wherein the heat and moisture exchanger adaptor is releasably engageable with the heat and moisture exchanger;
wherein the heat and moisture exchanger adaptor comprises:
a base having a first end in communication with the closed suction catheter assembly, and a second end configured for engaging the heat and moisture exchanger and positioning the closed suction catheter assembly with respect to the heat and moisture exchanger;
a retaining structure configured with the base to releasably engage the base with the heat and moisture exchanger;
a channel defined through the base so that the catheter of the closed suction catheter assembly is movable through the base and the heat and moisture exchanger and into an artificial airway connected to the heat and moisture exchanger; and
wherein the retaining structure comprises a first wall and a second wall, each of the walls having an aperture capable of selectively engaging projections extending outwardly from the heat and moisture exchanger.

29. A closed suction catheter system comprising:
a closed suction catheter assembly having a catheter and a protective sleeve enveloping the catheter, the closed suction catheter assembly including a distal end;
a heat and moisture exchanger, the catheter advanceable through the heat and moisture exchanger; and
a heat and moisture exchanger adaptor disposed at the distal end of the closed suction catheter assembly, wherein the heat and moisture exchanger adaptor is releasably engageable with the heat and moisture exchanger;
wherein the heat and moisture exchanger adaptor comprises:
a base having a first end in communication with the closed suction catheter assembly, and a second end configured for engaging the heat and moisture exchanger and positioning the closed suction catheter assembly with respect to the heat and moisture exchanger;
a retaining structure configured with the base to releasably engage the base with the heat and moisture exchanger;
a channel defined through the base so that the catheter of the closed suction catheter assembly is movable through the base and the heat and moisture exchanger and into an artificial airway connected to the heat and moisture exchanger; and
wherein the retaining structure comprises a retaining ring having apertures formed therein capable of engaging the heat and moisture exchanger.

30. A closed suction catheter system comprising:
- a closed suction catheter assembly having a catheter and a protective sleeve enveloping the catheter, the closed suction catheter assembly including a distal end;
- a heat and moisture exchanger, the catheter advanceable through the heat and moisture exchanger; and
- a heat and moisture exchanger adaptor disposed at the distal end of the closed suction catheter assembly, wherein the heat and moisture exchanger adaptor is releasably engageable with the heat and moisture exchanger;
- wherein the heat and moisture exchanger adaptor comprises:
  - a base having a first end in communication with the closed suction catheter assembly, and a second end configured for engaging the heat and moisture exchanger and positioning the closed suction catheter assembly with respect to the heat and moisture exchanger;
  - a retaining structure configured with the base to releasably engage the base with the heat and moisture exchanger;
  - a channel defined through the base so that the catheter of the closed suction catheter assembly is movable through the base and the heat and moisture exchanger and into an artificial airway connected to the heat and moisture exchanger; and
- means for disengaging the heat and moisture exchanger from the adaptor.

* * * * *

UNITED STATES PATENT AND TRADEMARK OFFICE
CERTIFICATE OF CORRECTION

PATENT NO. : 6,769,430 B1
DATED : August 3, 2004
INVENTOR(S) : Wayne D. Carlsen and Chet M. Crump It is certified that error appears in the above-identified patent and that said Letters Patent is hereby corrected as shown below:

<u>Column 12,</u>
Line 54, change "12" to -- 11 --.

Signed and Sealed this

Twenty-eighth Day of December, 2004

JON W. DUDAS
*Director of the United States Patent and Trademark Office*